US008859275B2

(12) United States Patent
Notka et al.

(10) Patent No.: US 8,859,275 B2
(45) Date of Patent: Oct. 14, 2014

(54) METHOD FOR MODULATING GENE EXPRESSION BY MODIFYING THE CPG CONTENT

(75) Inventors: Frank Notka, Regensburg (DE); Marcus Graf, Regensburg (DE); Doris Leikam, Regensburg (DE); Ralf Wagner, Regensburg (DE); David Raab, Beratzhausen (DE)

(73) Assignee: GeneArt AG, Regensburg (DE)

( * ) Notice: Subject to any disclaimer, the term of this patent is extended or adjusted under 35 U.S.C. 154(b) by 1748 days.

(21) Appl. No.: 11/659,315

(22) PCT Filed: Aug. 3, 2005

(86) PCT No.: PCT/EP2005/008423
§ 371 (c)(1),
(2), (4) Date: Feb. 2, 2007

(87) PCT Pub. No.: WO2006/015789
PCT Pub. Date: Feb. 16, 2006

(65) Prior Publication Data
US 2009/0324546 A1 Dec. 31, 2009

(30) Foreign Application Priority Data

Aug. 3, 2004 (DE) .......................... 10 2004 037 611
Aug. 3, 2004 (DE) .......................... 10 2004 037 652

(51) Int. Cl.
| | | |
|---|---|---|
| C12N 15/00 | (2006.01) | |
| C12N 15/87 | (2006.01) | |
| A61K 48/00 | (2006.01) | |
| C07H 21/04 | (2006.01) | |
| C07H 21/02 | (2006.01) | |
| C12N 15/63 | (2006.01) | |

(52) U.S. Cl.
CPC ...................................... *C12N 15/63* (2013.01)
USPC ....... 435/320.1; 435/463; 514/44 R; 536/23.1

(58) Field of Classification Search
None
See application file for complete search history.

(56) References Cited

U.S. PATENT DOCUMENTS

| | | | | |
|---|---|---|---|---|
| 7,569,553 | B2 * | 8/2009 | Krieg ........................... | 514/44 R |
| 7,576,066 | B2 * | 8/2009 | Krieg ........................... | 514/44 R |
| 7,605,138 | B2 * | 10/2009 | Krieg ........................... | 514/44 R |
| 8,224,578 | B2 * | 7/2012 | Raab et al. ...................... | 702/19 |
| 8,691,533 | B2 * | 4/2014 | Notka et al. ................... | 435/69.7 |
| 2003/0212026 | A1 * | 11/2003 | Krieg et al. ..................... | 514/44 |
| 2009/0324546 | A1 * | 12/2009 | Notka et al. ................... | 424/93.2 |
| 2013/0123483 | A1 * | 5/2013 | Raab et al. .................... | 536/23.2 |

FOREIGN PATENT DOCUMENTS

| | | |
|---|---|---|
| DE | 10053781 | 5/2002 |
| EP | 1156112 | 11/2001 |
| JP | 4550115 | 7/2010 |
| SG | 130229 | 2/2008 |
| WO | WO01/68824 | 9/2001 |
| WO | WO02/081677 | 10/2002 |
| WO | WO-02/099105 A2 | 12/2002 |
| WO | WO 2004/059556 A2 * | 7/2004 |
| ZA | 20070074 | 3/2008 |

OTHER PUBLICATIONS

Deml e tal, J. Virology, Nov. 2001, 75/22:10991-11001.*
Krieg et al, Trends Microbiol., 1998, 6:23-27.*
Sasaki et al, Methods, 2003, 31:246-254.*
Robinson, Clinical Microbiology Newsletter, Feb. 1, 2000, 22/3:17-22.*
Ertl et al, Methods, 2003, 31:199-206.*
Davis, Current Opinion in Biotechnology, 1997, 8:635-640.*
Restifo et al, Gene Therapy, 2000, 7:89-92.*
Lu et al, Expert Rev. Vaccines, 2008, 7/2:175-191.*
Sato et al, Science, Jul. 19, 1996. 273:352-354.*
Akiyama, "Cell-Type-Specific Repression of the Maspin Gene is Disrupted Frequently by Demethylation at the Promoter Region in Gastric Intestinal Metaplasia and Cancer Cells", *The American Journal of Pathology*, vol. 163, Issue 5, Nov. 2003, 1911-1919.
Antequera, "Number of CpG Islands and Genes in Human and Mouse", *Proceedings of the National Academy of Sciences*, vol. 90, Issue 24, Dec. 15, 1993, 11995-11999.
Ausubel, "Percentage of Kodon Synonymous Usage and Frequency of Kodon Occurrence in Various Organisms", *Current Protocols in Molecular Biology* Chapter 2, 1994, A 1.8-A 1.9.
Bird, "DNA Methylation and the Frequency of CpG in Animal DNA", *Nucleic Acids Research* vol. 8, Issue 7, Apr. 11, 1980, 1499-1504.
Buetler et al., "Evolution of the Genome and the Genetic Code: Selection at the Dinucleotide Level by Methylation and Polyribonucleotide Cleavage," Proceedings of the National Academy of Sciences, vol. 86, Issue 1, Jan. 1989, 192-196.
Chevalier-Mariette, "CpG Content Affects Gene Silencing in Mice: Evidence from Novel Transgenes", *Genome Biology*, vol. 4, Issue 9, 2003, R53.1-53.11.
Choi, "In Vitro Methylation of Nuclear Respiratory Factor-1 Binding Site Suppresses the Promoter Activity of Mitochondrial Transcription Factor A", *Biochemical and Biophysical Research Communications*, vol. 314, Issue 1, Jan. 30, 2004, 118-122.
Deng, "Methylation in hMLH1 Promoter Interferes With Its Binding to Transcription Factor CBF and Inhibits Gene Expression", *Oncogene*, vol. 20, Issue 48, Oct. 25, 2001, 7120-7127.
Duan, "Mammalian Mutation Pressure, Synonymous Codon Choice and mRNA Degradation", *Journal of Molecular Evolution*, vol. 57, Issue 6, Dec. 2003, 694-701.
Gardiner-Garden, "CpG Islands in Vertebrate Genomes", *Journal of Molecular Biology*, vol. 196, Issue 2, Jul. 20, 1987, 261-282.
Gellersen et al., "Human Prolactin Gene Expression: Positive Correlation Between Site-Specific Methylation and Gene Activity in a Set of Human Lymphoid Cell Lines," Molecular Endocronology, vol. 4, Issue 12, Dec. 1990, 1874-1886.

(Continued)

*Primary Examiner* — Nita M Minnifield

(57) ABSTRACT

The invention relates to nucleic acid modifications for a directed expression modulation by the targeted insertion or removal of CpG dinucleotides. The invention also relates to modified nucleic acids and expression vectors.

17 Claims, 9 Drawing Sheets

(56) References Cited

OTHER PUBLICATIONS

Figure 1:
Figure 1:
Figure 1:
Figure 1:
Figure 1:
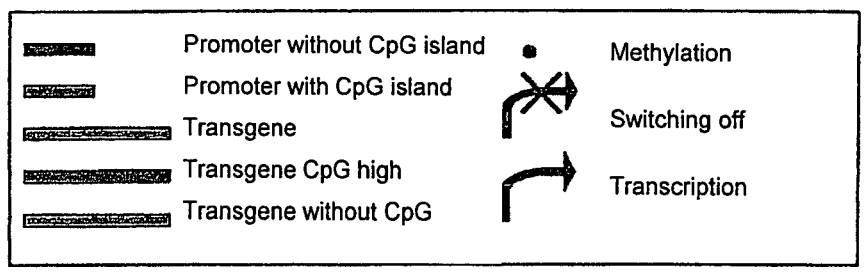

Graf, "Concerted Action of Multiple Cis-Acting Sequences is Required for Rev Dependence of Late Human Immunodeficiency Virus Type 1 Gene Expression", *Journal of Virology*, vol. 74, Issue 22, Nov. 2000, 10822-10826.

Hendrich, "Identification and Characterization of a Family of Mammalian Methyl-CpG Binding Proteins", *Molecular and Cellular Biology*, vol. 18, Issue 11, Nov. 1998, 6538-6547.

Hisano, "Methylation of CpG Dinucleotides in the Open Reading Frame of a Testicular Germ Cell-Specific Intronless Gene, Tract1/Acti7b, Represses the Expression of Somatic Cells", *Nucleic Acids Research*, vol. 31, Issue 6, Aug. 2003, 4797-4804.

Hsieh, "Dependence of Transcriptional Repression on CpG Methylation Density", *Molecular and Cell Biology*, vol. 14, Issue 8, Aug. 1994, 5487-5494.

Ivanova, "Frequent Hypermethylation of 5' Flanking Region of TIMP-2 Gene in Cervical Cancer", *International Journal of Cancer*, vol. 108, Issue 6, Mar. 1, 2004, 882-886.

Jones, "Methylated DNA and MeCP2 Recruit Histone Deacetylase to Repress Transcription", *Nature Genetics*, vol. 19, Issue 2, Jun. 1998, 187-191.

Kang, "Aberrant CpG Island Hypermethylation of Multiple Genes in Prostate Cancer and Prostatic Intraepithelial Neoplasia", *Journal of Pathology*, vol. 202. Issue 2, Feb. 2004, 233-240.

Kotsopoulou, "A Rev-Independent Human Immunodeficiency Virus Type 1 (HIV-1)-Based Vector That Exploits a Codon-Optimized HIV-1 Gag-Pol Gene", *Journal of Virology*, vol. 74, Issue 10, 2000, 4839-4852.

Kudo, "Methyl-CpG-Binding Protein MeCP2 Represses Sp1-Activated Transcription of the Human Leukosialin Gene When the Promoter Is Methylated", *Molecular and Cell Biology*, vol. 18, Issue 9, Sep. 1998, 5492-5499.

Laemmli, "Cleavage of Structural Proteins during the Assembly of the Head of Bacteriophage T4", *Nature*, vol. 227, Issue 5259, Aug. 15, 1970, 680-685.

Larsen, "CpG Islands as Gene Markers in the Human Genome", *Genomics* vol. 13, Issue 4, Aug. 1992, 1095-1107.

Li, "Transcriptional Silencing of the RUNX3 Gene by CpG Hypermethylation is Associated with Lung Cancer", *Biochemical and Biophysical Research Communications*, vol. 314, Issue 1, Jan. 30, 2004, 223-228.

Nan, "Transcriptional Repression by the Methyl-CpG-Binding Protein MeCP2 Involves a Histone Deacetylase Complex", *Nature*, vol. 393, May 28, 1998, 386-389.

International Application No. PCTEP2005008423, International Preliminary Examination Report dated Nov. 9, 2006.

International Application No. PCTEP2005008423, International Search Report dated Apr. 4, 2006.

International Application No. PCTEP2005008423, Written Opinion mailed Apr. 4, 2006.

Raab, Entwicklung eines integrierten Softwarepaketes zur Unterstützung des Designs and der Synthese artifizieller Gene in einer Hochdurchsatz-Umgebung, Ph.D. Thesis, 2003.

Shen, "The Rate of Hydrolytic Deamination of 5-Methylcytosine in Double-Stranded DNA", *Nucleic Acids Research*, vol. 22, Issue 6, Mar. 25, 1994, 972-976.

Sved, "The Expected Equlibrium of the CpG Dinucleotide in Vertebrate Genomes Under a Mutation Model", *Proceedings of the National Academy of Sciences*, vol. 87, Issue 12, Jun. 1990, 4692-4696.

Takai, "Comprehensive Analysis of CpG Islands in Human Chromosomes 21 and 22", *Proceedings of the National Academy of Sciences*, vol. 99, Issue 6, Mar. 19, 2002, 3740-3745.

Thanos et al., "DRD2 Gene Transfer Into the Nucleus Accumbens Core of the Alcohol Preferring and Nonpreferring Rats Attenuates Alcohol Drinking", Alcohol Clinical Experimental Research, vol. 28, Issue 8, May 2004, 720-726.

Voo, "Cloning of a Mammalian Transcriptional Activator That Binds Unmethylated CpG Motifs and Shares a CXXC Domain with DNA Methyltransferase, Human Trithorax, Methyl-CpG Binding Domain Protein 1", *Molecular and Cellular Biology*, vol. 20, Issue 6, Mar. 2000, 2108-2121.

Wade, "Mi-2 Complex Couples DNA Methylation to Chromatin Remodeling and Histone Deacetylation", *Nature Genetics*, vol. 23, 1999, 62-66.

Wise, "The Undermethylated State of a CpG Island Region in igf2 Transgenes is Dependent on the H19 Enhancers", *Genomics*, vol. 60, Issue 3, Sep. 15, 1999, 258-271.

Wolf, "Production, Mapping, and Biological Characterisation of Monoclonal Antibodies to the Core Protein (p24) of the Human Immunodeficiency Virus Type 1", *AIFO 1*, AIDS-Forsch, vol. 1, 1990, 24-29.

Wu, "5'-CpG Island Methylation of the FHIT Gene is Associated with Reduced Protein Expression and Higher Clinical State in Cervical Carcinomas", *Ultrastruct. Pathology*, vol. 27, Issue 6, Nov.-Dec. 2003, 417-422.

Yao, "A Methylated Oligonucleotide Inhibits IGF2 Expression and Enhances Survival in a Model of Hepatocellular Carcinoma", *Journal of Clinical Investigation*, vol. 111, Issue 2, Jan. 2003, 265-273.

Yoshida, "Aberrant Expression of the MEL1S Gene Identified in Association with Hypomethylation in Adult T-Cell Leukemia Cells", *Blood*, vol. 103, Issue 7, Apr. 1, 2004, 2753-2760.

Kanaya et al., "Codon Usage and tRNA Genes in Eurkaryotes: Correlation of Codon Usage Diversity with Translation Efficiency and with CG-Dinucleotide Usage Assessed by Multivariate Analysis", *Journal of Molecular Evolution*, vol. 53, Nos. 4-5, Oct.-Nov. 2001, 290-298.

\* cited by examiner

A

B

C

D

SEQUENCE LISTING

```
<160> NUMBER OF SEQ ID NOS: 59

<210> SEQ ID NO 1
<211> LENGTH: 720
<212> TYPE: DNA
<213> ORGANISM: Artificial Sequence
<220> FEATURE:
<221> NAME/KEY: CDS
<222> LOCATION: (1)..(720)
<223> OTHER INFORMATION: Depleted delta green fluorescent protein (GFP)
      gene

<400> SEQUENCE: 1 atg gtg tcc aag ggg gag gag ctg ttc aca ggg gtg gtg ccc atc ctg         48
Met Val Ser Lys Gly Glu Glu Leu Phe Thr Gly Val Val Pro Ile Leu
 1               5                  10                  15 gtg gag ctg gat ggg gat gtg aat ggc cac aag ttc tct gtg tct ggg         96
Val Glu Leu Asp Gly Asp Val Asn Gly His Lys Phe Ser Val Ser Gly
             20                  25                  30 gag ggg gag ggg gat gcc acc tat ggc aag ctc acc ctg aag ttc atc        144
Glu Gly Glu Gly Asp Ala Thr Tyr Gly Lys Leu Thr Leu Lys Phe Ile
         35                  40                  45 tgc acc aca ggc aag ctg cca gtg ccc tgg ccc acc ctg gtg acc acc        192
Cys Thr Thr Gly Lys Leu Pro Val Pro Trp Pro Thr Leu Val Thr Thr
     50                  55                  60 ttc acc tat ggg gtg cag tgc ttc agc aga tac cca gac cac atg aag        240
Phe Thr Tyr Gly Val Gln Cys Phe Ser Arg Tyr Pro Asp His Met Lys
 65                  70                  75                  80 cag cat gac ttc ttc aag tct gcc atg cct gag ggc tat gtg cag gag        288
Gln His Asp Phe Phe Lys Ser Ala Met Pro Glu Gly Tyr Val Gln Glu
                 85                  90                  95 agg acc atc ttc ttc aag gat gat ggc aac tac aag acc agg gct gag        336
Arg Thr Ile Phe Phe Lys Asp Asp Gly Asn Tyr Lys Thr Arg Ala Glu
            100                 105                 110 gtg aag ttt gag ggg gat acc ctg gtg aac agg att gag ctg aag ggc        384
Val Lys Phe Glu Gly Asp Thr Leu Val Asn Arg Ile Glu Leu Lys Gly
        115                 120                 125 att gac ttt aag gag gat ggc aat atc ctg ggc cac aag ctg gag tac        432
Ile Asp Phe Lys Glu Asp Gly Asn Ile Leu Gly His Lys Leu Glu Tyr
    130                 135                 140 aac tac aac agc cac aat gtg tac atc atg gca gac aag cag aag aat        480
Asn Tyr Asn Ser His Asn Val Tyr Ile Met Ala Asp Lys Gln Lys Asn
145                 150                 155                 160 ggc atc aag gtg aac ttc aag atc agg cac aac att gag gat ggc tct        528
Gly Ile Lys Val Asn Phe Lys Ile Arg His Asn Ile Glu Asp Gly Ser
                165                 170                 175 gtg cag ctg gca gac cac tac cag cag aac acc ccc att gga gat ggc        576
Val Gln Leu Ala Asp His Tyr Gln Gln Asn Thr Pro Ile Gly Asp Gly
            180                 185                 190 cct gtc ctg ctg cca gac aac cac tac ctg agc acc cag tct gcc ctg        624
Pro Val Leu Leu Pro Asp Asn His Tyr Leu Ser Thr Gln Ser Ala Leu
        195                 200                 205
```

```
agc aag gac ccc aat gag aag agg gac cac atg gtg ctg ctg gag ttt      672
Ser Lys Asp Pro Asn Glu Lys Arg Asp His Met Val Leu Leu Glu Phe
    210                 215                 220 gtg aca gct gct ggc atc acc ctg ggc atg gat gag ctg tac aag tga      720
Val Thr Ala Ala Gly Ile Thr Leu Gly Met Asp Glu Leu Tyr Lys
225                 230                 235                 240
```

<210> SEQ ID NO 2
<211> LENGTH: 239
<212> TYPE: PRT
<213> ORGANISM: Artificial sequence
<220> FEATURE:
<223> OTHER INFORMATION: Depleted delta green fluorescent protein (GFP) gene

<400> SEQUENCE: 2

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Phe Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 3
<211> LENGTH: 720
<212> TYPE: DNA
<213> ORGANISM: Artificial sequence
<220> FEATURE:
<221> NAME/KEY: CDS
<222> LOCATION: (1)..(720)
<223> OTHER INFORMATION: Depleted human delta green fluorescent protein (huGFP) gene

```
<400> SEQUENCE: 3 atg gtg agc aag ggc gag gag ctg ttc acc ggg gtg gtg ccc atc ctg     48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc     96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
50                  55                  60 ttc acc tac ggc gtg cag tgc ttc agc cgc tac ccc gac cac atg aag    240
Phe Thr Tyr Gly Val Gln Cys Phe Ser Arg Tyr Pro Asp His Met Lys
 65                 70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac    480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc    576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg    624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc    672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa    720
Val Thr Ala Ala Gly Ile Thr Leu Gly Met Asp Glu Leu Tyr Lys
225                 230                 235

<210> SEQ ID NO 4
<211> LENGTH: 239
<212> TYPE: PRT
<213> ORGANISM: Artificial sequence
<220> FEATURE:
<223> OTHER INFORMATION: Depleted human delta green fluorescent protein
      (huGFP) gene

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30
```

```
Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Phe Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
             100                 105                 110

Val Lys Phe Glu Gly Asp Thr Leu Val Asn Arg Ile Glu Leu Lys Gly
         115                 120                 125

Ile Asp Phe Lys Glu Asp Gly Asn Ile Leu Gly His Lys Leu Glu Tyr
 130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                 165                 170                 175

Val Gln Leu Ala Asp His Tyr Gln Gln Asn Thr Pro Ile Gly Asp Gly
             180                 185                 190

Pro Val Leu Leu Pro Asp Asn His Tyr Leu Ser Thr Gln Ser Ala Leu
         195                 200                 205

Ser Lys Asp Pro Asn Glu Lys Arg Asp His Met Val Leu Leu Glu Phe
 210                 215                 220

Val Thr Ala Ala Gly Ile Thr Leu Gly Met Asp Glu Leu Tyr Lys
225                 230                 235

<210> SEQ ID NO 5
<211> LENGTH: 279
<212> TYPE: DNA
<213> ORGANISM: Artificial sequence
<220> FEATURE:
<221> NAME/KEY: CDS
<222> LOCATION: (1)..(279)
<223> OTHER INFORMATION: Portion of murine MIP1alpha-0CpG (murine
      MIP1alpha gene with 0 CpG dinucleotides)

<400> SEQUENCE: 5 atg aag gtg agc aca aca gct ctg gct gtg ctg ctg tgt acc atg acc      48
Met Lys Val Ser Thr Thr Ala Leu Ala Val Leu Leu Cys Thr Met Thr
 1               5                  10                  15 ctg tgc aac cag gtg ttc tct gcc cct tat gga gca gat acc cct aca      96
Leu Cys Asn Gln Val Phe Ser Ala Pro Tyr Gly Ala Asp Thr Pro Thr
             20                  25                  30 gcc tgc tgt ttc agc tac agc agg aag atc ccc agg cag ttc att gtg     144
Ala Cys Cys Phe Ser Tyr Ser Arg Lys Ile Pro Arg Gln Phe Ile Val
         35                  40                  45 gac tac ttt gag acc agc agc ctg tgt tct cag cct ggg gtg atc ttt     192
Asp Tyr Phe Glu Thr Ser Ser Leu Cys Ser Gln Pro Gly Val Ile Phe
 50                  55                  60 ctg acc aag agg aac agg cag atc tgt gca gac agc aag gag aca tgg     240
Leu Thr Lys Arg Asn Arg Gln Ile Cys Ala Asp Ser Lys Glu Thr Trp
 65                  70                  75                  80 gtg cag gag tac atc aca gac ctg gag ctg aat gcc tag                 279
Val Gln Glu Tyr Ile Thr Asp Leu Glu Leu Asn Ala
                 85                  90
```

-continued

```
<210> SEQ ID NO 6
<211> LENGTH: 92
<212> TYPE: PRT
<213> ORGANISM: Artificial sequence
<220> FEATURE:
<223> OTHER INFORMATION: Portion of murine MIP1alpha-0CpG (murine
      MIP1alpha gene with 0 CpG dinucleotides)

<400> SEQUENCE: 6

Met Lys Val Ser Thr Thr Ala Leu Ala Val Leu Leu Cys Thr Met Thr
 1               5                  10                  15

Leu Cys Asn Gln Val Phe Ser Ala Pro Tyr Gly Ala Asp Thr Pro Thr
             20                  25                  30

Ala Cys Cys Phe Ser Tyr Ser Arg Lys Ile Pro Arg Gln Phe Ile Val
         35                  40                  45

Asp Tyr Phe Glu Thr Ser Ser Leu Cys Ser Gln Pro Gly Val Ile Phe
     50                  55                  60

Leu Thr Lys Arg Asn Arg Gln Ile Cys Ala Asp Ser Lys Glu Thr Trp
 65                  70                  75                  80

Val Gln Glu Tyr Ile Thr Asp Leu Glu Leu Asn Ala
                 85                  90

<210> SEQ ID NO 7
<211> LENGTH: 279
<212> TYPE: DNA
<213> ORGANISM: Artificial sequence
<220> FEATURE:
<221> NAME/KEY: CDS
<222> LOCATION: (1)..(279)
<223> OTHER INFORMATION: Portion of murine MIP1alpha-2CpG (murine
      MIP1alpha gene with 2 CpG dinucleotides)

<400> SEQUENCE: 7 atg aag gtg agc aca aca gct ctg gcc gtg ctg ctg tgt acc atg acc       48
Met Lys Val Ser Thr Thr Ala Leu Ala Val Leu Leu Cys Thr Met Thr
 1               5                  10                  15 ctg tgc aac cag gtg ttc tct gcc cct tat gga gca gat acc cct aca       96
Leu Cys Asn Gln Val Phe Ser Ala Pro Tyr Gly Ala Asp Thr Pro Thr
             20                  25                  30 gcc tgc tgt ttc agc tac agc agg aag atc ccc agg cag ttc atc gtg      144
Ala Cys Cys Phe Ser Tyr Ser Arg Lys Ile Pro Arg Gln Phe Ile Val
         35                  40                  45 gac tac ttt gag acc agc agc ctg tgt tct cag cct ggg gtg atc ttt      192
Asp Tyr Phe Glu Thr Ser Ser Leu Cys Ser Gln Pro Gly Val Ile Phe
     50                  55                  60 ctg acc aag agg aac agg cag atc tgt gca gac agc aag gag aca tgg      240
Leu Thr Lys Arg Asn Arg Gln Ile Cys Ala Asp Ser Lys Glu Thr Trp
 65                  70                  75                  80 gtg cag gag tac atc aca gac ctg gag ctg aat gcc tag                  279
Val Gln Glu Tyr Ile Thr Asp Leu Glu Leu Asn Ala
                 85                  90

<210> SEQ ID NO 8
<211> LENGTH: 92
<212> TYPE: PRT
<213> ORGANISM: Artificial sequence
<220> FEATURE:
<223> OTHER INFORMATION: Portion of murine MIP1alpha-2CpG (murine
      MIP1alpha gene with 2 CpG dinucleotides)

<400> SEQUENCE: 8

Met Lys Val Ser Thr Thr Ala Leu Ala Val Leu Leu Cys Thr Met Thr
 1               5                  10                  15
```

```
Leu Cys Asn Gln Val Phe Ser Ala Pro Tyr Gly Ala Asp Thr Pro Thr
            20                  25                  30

Ala Cys Cys Phe Ser Tyr Ser Arg Lys Ile Pro Arg Gln Phe Ile Val
        35                  40                  45

Asp Tyr Phe Glu Thr Ser Ser Leu Cys Ser Gln Pro Gly Val Ile Phe
    50                  55                  60

Leu Thr Lys Arg Asn Arg Gln Ile Cys Ala Asp Ser Lys Glu Thr Trp
65                  70                  75                  80

Val Gln Glu Tyr Ile Thr Asp Leu Glu Leu Asn Ala
                85                  90

<210> SEQ ID NO 9
<211> LENGTH: 279
<212> TYPE: DNA
<213> ORGANISM: Artificial sequence
<220> FEATURE:
<221> NAME/KEY: CDS
<222> LOCATION: (1)..(279)
<223> OTHER INFORMATION: Portion of murine MIP1alpha-4CpG (murine
      MIP1alpha gene with 4 CpG dinucleotides)

<400> SEQUENCE: 9 atg aag gtg agc aca aca gct ctg gcc gtg ctg ctg tgt acc atg acc      48
Met Lys Val Ser Thr Thr Ala Leu Ala Val Leu Leu Cys Thr Met Thr
1               5                   10                  15 ctg tgc aac cag gtg ttc tct gcc cct tac gga gca gat acc cct aca      96
Leu Cys Asn Gln Val Phe Ser Ala Pro Tyr Gly Ala Asp Thr Pro Thr
            20                  25                  30 gcc tgc tgt ttc agc tac agc agg aag atc ccc agg cag ttc atc gtg     144
Ala Cys Cys Phe Ser Tyr Ser Arg Lys Ile Pro Arg Gln Phe Ile Val
        35                  40                  45 gac tac ttt gag acc agc agc ctg tgt tct cag cct ggg gtg atc ttt     192
Asp Tyr Phe Glu Thr Ser Ser Leu Cys Ser Gln Pro Gly Val Ile Phe
    50                  55                  60 ctg acc aag agg aac cgc cag atc tgt gca gac agc aag gag aca tgg     240
Leu Thr Lys Arg Asn Arg Gln Ile Cys Ala Asp Ser Lys Glu Thr Trp
65                  70                  75                  80 gtg cag gag tac atc aca gac ctg gag ctg aat gcc tag                 279
Val Gln Glu Tyr Ile Thr Asp Leu Glu Leu Asn Ala
                85                  90

<210> SEQ ID NO 10
<211> LENGTH: 92
<212> TYPE: PRT
<213> ORGANISM: Artificial sequence
<220> FEATURE:
<223> OTHER INFORMATION: Portion murine MIP1alpha-4CpG (murine
      MIP1alpha gene with 4 CpG dinucleotides)

<400> SEQUENCE: 10

Met Lys Val Ser Thr Thr Ala Leu Ala Val Leu Leu Cys Thr Met Thr
1               5                   10                  15

Leu Cys Asn Gln Val Phe Ser Ala Pro Tyr Gly Ala Asp Thr Pro Thr
            20                  25                  30

Ala Cys Cys Phe Ser Tyr Ser Arg Lys Ile Pro Arg Gln Phe Ile Val
        35                  40                  45

Asp Tyr Phe Glu Thr Ser Ser Leu Cys Ser Gln Pro Gly Val Ile Phe
    50                  55                  60

Leu Thr Lys Arg Asn Arg Gln Ile Cys Ala Asp Ser Lys Glu Thr Trp
65                  70                  75                  80

Val Gln Glu Tyr Ile Thr Asp Leu Glu Leu Asn Ala
```

<210> SEQ ID NO 11
<211> LENGTH: 279
<212> TYPE: DNA
<213> ORGANISM: Artificial sequence
<220> FEATURE:
<221> NAME/KEY: CDS
<222> LOCATION: (1)..(279)
<223> OTHER INFORMATION: Portion of murine MIP1alpha-13CpG (murine MIP1alpha gene with 13 CpG dinucleotides)

<400> SEQUENCE: 11

```
atg aag gtg agc acc aca gct ctg gct gtg ctg ctg tgc acc atg acc      48
Met Lys Val Ser Thr Thr Ala Leu Ala Val Leu Leu Cys Thr Met Thr
 1               5                  10                  15 ctg tgc aac cag gtg ttc agc gct cct tac ggc gcc gat acc cct aca      96
Leu Cys Asn Gln Val Phe Ser Ala Pro Tyr Gly Ala Asp Thr Pro Thr
             20                  25                  30 gcc tgc tgc ttc agc tac agc agg aag atc ccc agg cag ttc atc gtg     144
Ala Cys Cys Phe Ser Tyr Ser Arg Lys Ile Pro Arg Gln Phe Ile Val
         35                  40                  45 gac tac ttc gag acc agc agc ctg tgt tct cag ccc ggc gtg atc ttc     192
Asp Tyr Phe Glu Thr Ser Ser Leu Cys Ser Gln Pro Gly Val Ile Phe
     50                  55                  60 ctg acc aag cgg aac aga cag atc tgc gcc gac agc aag gag aca tgg     240
Leu Thr Lys Arg Asn Arg Gln Ile Cys Ala Asp Ser Lys Glu Thr Trp
 65                  70                  75                  80 gtg cag gag tac atc acc gac ctg gag ctg aac gcc tag                 279
Val Gln Glu Tyr Ile Thr Asp Leu Glu Leu Asn Ala
                 85                  90
```

<210> SEQ ID NO 12
<211> LENGTH: 92
<212> TYPE: PRT
<213> ORGANISM: Artificial sequence
<220> FEATURE:
<223> OTHER INFORMATION: Portion of murine MIP1alpha-13CpG (murine MIP1alpha gene with 13 CpG dinucleotides)

<400> SEQUENCE: 12

```
Met Lys Val Ser Thr Thr Ala Leu Ala Val Leu Leu Cys Thr Met Thr
 1               5                  10                  15

Leu Cys Asn Gln Val Phe Ser Ala Pro Tyr Gly Ala Asp Thr Pro Thr
             20                  25                  30

Ala Cys Cys Phe Ser Tyr Ser Arg Lys Ile Pro Arg Gln Phe Ile Val
         35                  40                  45

Asp Tyr Phe Glu Thr Ser Ser Leu Cys Ser Gln Pro Gly Val Ile Phe
     50                  55                  60

Leu Thr Lys Arg Asn Arg Gln Ile Cys Ala Asp Ser Lys Glu Thr Trp
 65                  70                  75                  80

Val Gln Glu Tyr Ile Thr Asp Leu Glu Leu Asn Ala
                 85                  90
```

<210> SEQ ID NO 13
<211> LENGTH: 279
<212> TYPE: DNA
<213> ORGANISM: Artificial sequence
<220> FEATURE:
<221> NAME/KEY: CDS
<222> LOCATION: (1)..(279)
<223> OTHER INFORMATION: Portion of murine MIP1alpha-42CpG (murine MIP1alpha gene with 42 CpG dinucleotides)

<400> SEQUENCE: 13

```
atg aag gtg tcg acg acc gcg ctc gcc gtg ctg ctg tgc acg atg acg      48
Met Lys Val Ser Thr Thr Ala Leu Ala Val Leu Leu Cys Thr Met Thr
 1               5                  10                  15 ctg tgc aac cag gtg ttc agc gcc ccg tac ggc gcc gac acg ccg acc      96
Leu Cys Asn Gln Val Phe Ser Ala Pro Tyr Gly Ala Asp Thr Pro Thr
             20                  25                  30 gcg tgc tgc ttc tcg tac tcg cgg aag atc ccg cgg cag ttc atc gtc     144
Ala Cys Cys Phe Ser Tyr Ser Arg Lys Ile Pro Arg Gln Phe Ile Val
         35                  40                  45 gac tac ttc gaa acg tcg tcg ctg tgc tcg cag ccc ggc gtg atc ttc     192
Asp Tyr Phe Glu Thr Ser Ser Leu Cys Ser Gln Pro Gly Val Ile Phe
     50                  55                  60 ctc acg aag cgg aac cgg cag atc tgc gcc gac tcg aag gaa acg tgg     240
Leu Thr Lys Arg Asn Arg Gln Ile Cys Ala Asp Ser Lys Glu Thr Trp
 65                  70                  75                  80 gtg cag gag tac atc acc gac ctc gaa ctg aac gcg tag                 279
Val Gln Glu Tyr Ile Thr Asp Leu Glu Leu Asn Ala
                 85                  90
```

<210> SEQ ID NO 14
<211> LENGTH: 92
<212> TYPE: PRT
<213> ORGANISM: Artificial sequence
<220> FEATURE:
<223> OTHER INFORMATION: Portion of murine MIP1alpha-42CpG (murine MIP1alpha gene with 42 CpG dinucleotides)

<400> SEQUENCE: 14

```
Met Lys Val Ser Thr Thr Ala Leu Ala Val Leu Leu Cys Thr Met Thr
 1               5                  10                  15

Leu Cys Asn Gln Val Phe Ser Ala Pro Tyr Gly Ala Asp Thr Pro Thr
             20                  25                  30

Ala Cys Cys Phe Ser Tyr Ser Arg Lys Ile Pro Arg Gln Phe Ile Val
         35                  40                  45

Asp Tyr Phe Glu Thr Ser Ser Leu Cys Ser Gln Pro Gly Val Ile Phe
     50                  55                  60

Leu Thr Lys Arg Asn Arg Gln Ile Cys Ala Asp Ser Lys Glu Thr Trp
 65                  70                  75                  80

Val Gln Glu Tyr Ile Thr Asp Leu Glu Leu Asn Ala
                 85                  90
```

<210> SEQ ID NO 15
<211> LENGTH: 279
<212> TYPE: DNA
<213> ORGANISM: Mus musculus
<220> FEATURE:
<221> NAME/KEY: CDS
<222> LOCATION: (1)..(279)

<400> SEQUENCE: 15

```
atg aag gtc tcc acc act gcc ctt gct gtt ctt ctc tgt acc atg aca      48
Met Lys Val Ser Thr Thr Ala Leu Ala Val Leu Leu Cys Thr Met Thr
 1               5                  10                  15 ctc tgc aac caa gtc ttc tca gcg cca tat gga gct gac acc ccg act      96
Leu Cys Asn Gln Val Phe Ser Ala Pro Tyr Gly Ala Asp Thr Pro Thr
             20                  25                  30 gcc tgc tgc ttc tcc tac agc cgg aag att cca cgc caa ttc atc gtt     144
Ala Cys Cys Phe Ser Tyr Ser Arg Lys Ile Pro Arg Gln Phe Ile Val
         35                  40                  45 gac tat ttt gaa acc agc agc ctt tgc tcc cag cca ggt gtc att ttc     192
```

```
Asp Tyr Phe Glu Thr Ser Ser Leu Cys Ser Gln Pro Gly Val Ile Phe
         50                  55                  60 ctg act aag aga aac cgg cag atc tgc gct gac tcc aaa gag acc tgg      240
Leu Thr Lys Arg Asn Arg Gln Ile Cys Ala Asp Ser Lys Glu Thr Trp
 65                  70                  75                  80 gtc caa gaa tac atc act gac ctg gaa ctg aat gcc tag                  279
Val Gln Glu Tyr Ile Thr Asp Leu Glu Leu Asn Ala
                 85                  90
```

<210> SEQ ID NO 16
<211> LENGTH: 92
<212> TYPE: PRT
<213> ORGANISM: Mus musculus
<220> FEATURE:

<400> SEQUENCE: 16

```
Met Lys Val Ser Thr Thr Ala Leu Ala Val Leu Leu Cys Thr Met Thr
 1               5                  10                  15

Leu Cys Asn Gln Val Phe Ser Ala Pro Tyr Gly Ala Asp Thr Pro Thr
                 20                  25                  30

Ala Cys Cys Phe Ser Tyr Ser Arg Lys Ile Pro Arg Gln Phe Ile Val
             35                  40                  45

Asp Tyr Phe Glu Thr Ser Ser Leu Cys Ser Gln Pro Gly Val Ile Phe
         50                  55                  60

Leu Thr Lys Arg Asn Arg Gln Ile Cys Ala Asp Ser Lys Glu Thr Trp
 65                  70                  75                  80

Val Gln Glu Tyr Ile Thr Asp Leu Glu Leu Asn Ala
                 85                  90
```

<210> SEQ ID NO 17
<211> LENGTH: 282
<212> TYPE: DNA
<213> ORGANISM: Artificial sequence
<220> FEATURE:
<221> NAME/KEY: CDS
<222> LOCATION: (1)..(282)
<223> OTHER INFORMATION: Portion of human MIP1alpha-43CpG (human
      MIP1alpha gene with 43 CpG)

<400> SEQUENCE: 17

```
atg caa gtg tcg acc gcc gct ctc gcc gtg ctg ctg tgc acg atg gcg       48
Met Gln Val Ser Thr Ala Ala Leu Ala Val Leu Leu Cys Thr Met Ala
 1               5                  10                  15 ctg tgc aac caa gtg ctg agc gcg cct ctc gcc gcc gac acg ccg acc       96
Leu Cys Asn Gln Val Leu Ser Ala Pro Leu Ala Ala Asp Thr Pro Thr
                 20                  25                  30 gcg tgc tgc ttc tcg tac acg tcg cgg cag atc ccg cag aac ttc atc      144
Ala Cys Cys Phe Ser Tyr Thr Ser Arg Gln Ile Pro Gln Asn Phe Ile
             35                  40                  45 gcc gac tac ttc gag acg tcg tcg cag tgc tcg aag ccg agc gtg atc      192
Ala Asp Tyr Phe Glu Thr Ser Ser Gln Cys Ser Lys Pro Ser Val Ile
         50                  55                  60 ttc ctg acg aag cgc gga cgg caa gtg tgc gcc gac ccg agc gag gag      240
Phe Leu Thr Lys Arg Gly Arg Gln Val Cys Ala Asp Pro Ser Glu Glu
 65                  70                  75                  80 tgg gtg cag aag tac gtg agc gac ctc gaa ctg agc gcg tag              282
Trp Val Gln Lys Tyr Val Ser Asp Leu Glu Leu Ser Ala
                 85                  90
```

<210> SEQ ID NO 18
<211> LENGTH: 93
<212> TYPE: PRT

```
<213> ORGANISM: Artificial sequence
<220> FEATURE:
<223> OTHER INFORMATION: Portion of human MIP1alpha-43cpg (human
      MIP1alpha gene with 43 CpG)

<400> SEQUENCE: 18

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90

<210> SEQ ID NO 19
<211> LENGTH: 435
<212> TYPE: DNA
<213> ORGANISM: Artificial sequence
<220> FEATURE:
<221> NAME/KEY: CDS
<222> LOCATION: (1)..(432)
<223> OTHER INFORMATION: Description of the artificial sequence:
      synthetic gene human GM-CSF-63CpG

<400> SEQUENCE: 19 atg tgg ctg cag tcg ctg ctg ctg ctc gga acc gtc gcg tgt tcg atc      48
Met Trp Leu Gln Ser Leu Leu Leu Leu Gly Thr Val Ala Cys Ser Ile
1               5                   10                  15 agc gcg cct gcg cgg tcg ccg tcg ccg tcg acg cag ccg tgg gag cac      96
Ser Ala Pro Ala Arg Ser Pro Ser Pro Ser Thr Gln Pro Trp Glu His
            20                  25                  30 gtg aac gcg atc cag gag gcg cga cgg ctg ctg aac ctg tcg cgc gat     144
Val Asn Ala Ile Gln Glu Ala Arg Arg Leu Leu Asn Leu Ser Arg Asp
        35                  40                  45 aca gcc gcc gag atg aac gag acc gtc gag gtg atc agc gag atg ttc     192
Thr Ala Ala Glu Met Asn Glu Thr Val Glu Val Ile Ser Glu Met Phe
    50                  55                  60 gac ctg cag gag ccg acg tgc ctg cag acg cgg ctc gaa ctg tat aag     240
Asp Leu Gln Glu Pro Thr Cys Leu Gln Thr Arg Leu Glu Leu Tyr Lys
65                  70                  75                  80 cag ggc ctc cgc ggc tcg ctc acg aag ctg aag ggc ccg ctc acg atg     288
Gln Gly Leu Arg Gly Ser Leu Thr Lys Leu Lys Gly Pro Leu Thr Met
                85                  90                  95 atg gcg tcg cac tac aag cag cac tgc ccg ccg acg ccc gaa acg tcg     336
Met Ala Ser His Tyr Lys Gln His Cys Pro Pro Thr Pro Glu Thr Ser
            100                 105                 110 tgc gcg acg cag atc atc acg ttc gag tcg ttc aag gag aac ctg aag     384
Cys Ala Thr Gln Ile Ile Thr Phe Glu Ser Phe Lys Glu Asn Leu Lys
        115                 120                 125 gac ttc ctg ctc gtg atc ccg ttc gat tgc tgg gag ccc gtg cag gag     432
Asp Phe Leu Leu Val Ile Pro Phe Asp Cys Trp Glu Pro Val Gln Glu
    130                 135                 140 tag                                                                  435

<210> SEQ ID NO 20
<211> LENGTH: 144
```

```
<212> TYPE: PRT
<213> ORGANISM: Artificial sequence
<220> FEATURE:
<223> OTHER INFORMATION: human GM-CSF-63CpG

<400> SEQUENCE: 20

Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
             20                  25                  30

Val Asn Ala Ile Gln Glu Ala Arg Arg Leu Leu Asn Leu Ser Arg Asp
         35                  40                  45

Thr Ala Ala Glu Met Asn Glu Thr Val Glu Val Ile Ser Glu Met Phe
     50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 21
<211> LENGTH: 282
<212> TYPE: DNA
<213> ORGANISM: Homo sapiens
<220> FEATURE:
<221> NAME/KEY: CDS
<222> LOCATION: (1)..(282)
<223> OTHER INFORMATION: human MIP1alpha gene wild-type (8CpG)

<400> SEQUENCE: 21 atg cag gtc tcc act gct gcc ctt gcc gtc ctc ctc tgc acc atg gct      48
Met Gln Val Ser Thr Ala Ala Leu Ala Val Leu Leu Cys Thr Met Ala
 1               5                  10                  15 ctc tgc aac cag gtc ctc tct gca cca ctt gct gct gac acg ccg acc      96
Leu Cys Asn Gln Val Leu Ser Ala Pro Leu Ala Ala Asp Thr Pro Thr
             20                  25                  30 gcc tgc tgc ttc agc tac acc tcc cga cag att cca cag aat ttc ata     144
Ala Cys Cys Phe Ser Tyr Thr Ser Arg Gln Ile Pro Gln Asn Phe Ile
         35                  40                  45 gct gac tac ttt gag acg agc agc cag tgc tcc aag ccc agt gtc atc     192
Ala Asp Tyr Phe Glu Thr Ser Ser Gln Cys Ser Lys Pro Ser Val Ile
     50                  55                  60 ttc cta acc aag aga ggc cgg cag gtc tgt gct gac ccc agt gag gag     240
Phe Leu Thr Lys Arg Gly Arg Gln Val Cys Ala Asp Pro Ser Glu Glu
 65                  70                  75                  80 tgg gtc cag aaa tac gtc agt gac ctg gag ctg agt gcc tag             282
Trp Val Gln Lys Tyr Val Ser Asp Leu Glu Leu Ser Ala
                 85                  90

<210> SEQ ID NO 22
<211> LENGTH: 93
<212> TYPE: PRT
<213> ORGANISM: Homo sapiens
<220> FEATURE:
<223> OTHER INFORMATION: human MIP1alpha gene wild-type (8CpG)

<400> SEQUENCE: 22
```

```
Met Gln Val Ser Thr Ala Ala Leu Ala Val Leu Leu Cys Thr Met Ala
  1               5                  10                  15

Leu Cys Asn Gln Val Leu Ser Ala Pro Leu Ala Ala Asp Thr Pro Thr
             20                  25                  30

Ala Cys Cys Phe Ser Tyr Thr Ser Arg Gln Ile Pro Gln Asn Phe Ile
         35                  40                  45

Ala Asp Tyr Phe Glu Thr Ser Ser Gln Cys Ser Lys Pro Ser Val Ile
     50                  55                  60

Phe Leu Thr Lys Arg Gly Arg Gln Val Cys Ala Asp Pro Ser Glu Glu
 65                  70                  75                  80

Trp Val Gln Lys Tyr Val Ser Asp Leu Glu Leu Ser Ala
                 85                  90

<210> SEQ ID NO 23
<211> LENGTH: 435
<212> TYPE: DNA
<213> ORGANISM: Homo sapiens
<220> FEATURE:
<221> NAME/KEY: CDS
<222> LOCATION: (1)..(432)
<223> OTHER INFORMATION: human GM-CSF gene wild-type (10CpG)

<400> SEQUENCE: 23 atg tgg ctg cag agc ctg ctg ctc ttg ggc act gtg gcc tgc agc atc      48
Met Trp Leu Gln Ser Leu Leu Leu Leu Gly Thr Val Ala Cys Ser Ile
  1               5                  10                  15 tct gca ccc gcc cgc tcg ccc agc ccc agc acg cag ccc tgg gag cat      96
Ser Ala Pro Ala Arg Ser Pro Ser Pro Ser Thr Gln Pro Trp Glu His
             20                  25                  30 gtg aat gcc atc cag gag gcc cgg cgt ctc ctg aac ctg agt aga gac     144
Val Asn Ala Ile Gln Glu Ala Arg Arg Leu Leu Asn Leu Ser Arg Asp
         35                  40                  45 act gct gct gag atg aat gaa aca gta gaa gtc atc tca gaa atg ttt     192
Thr Ala Ala Glu Met Asn Glu Thr Val Glu Val Ile Ser Glu Met Phe
     50                  55                  60 gac ctc cag gag ccg acc tgc cta cag acc cgc ctg gag ctg tac aag     240
Asp Leu Gln Glu Pro Thr Cys Leu Gln Thr Arg Leu Glu Leu Tyr Lys
 65                  70                  75                  80 cag ggc ctg cgg ggc agc ctc acc aag ctc aag ggc ccc ttg acc atg     288
Gln Gly Leu Arg Gly Ser Leu Thr Lys Leu Lys Gly Pro Leu Thr Met
                 85                  90                  95 atg gcc agc cac tac aag cag cac tgc cct cca acc ccg gaa act tcc     336
Met Ala Ser His Tyr Lys Gln His Cys Pro Pro Thr Pro Glu Thr Ser
            100                 105                 110 tgt gca acc cag att atc acc ttt gaa agt ttc aaa gag aac ctg aag     384
Cys Ala Thr Gln Ile Ile Thr Phe Glu Ser Phe Lys Glu Asn Leu Lys
        115                 120                 125 gac ttt ctg ctt gtc atc ccc ttt gac tgc tgg gag cca gtc cag gag     432
Asp Phe Leu Leu Val Ile Pro Phe Asp Cys Trp Glu Pro Val Gln Glu
    130                 135                 140 tag                                                                  435

<210> SEQ ID NO 24
<211> LENGTH: 144
<212> TYPE: PRT
<213> ORGANISM: Homo sapiens
<220> FEATURE:
<223> OTHER INFORMATION: human GM-CSF gene wild-type (10CpG)

<400> SEQUENCE: 24
```

```
Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 25
<211> LENGTH: 3034
<212> TYPE: DNA
<213> ORGANISM: Artificial sequence
<220> FEATURE:
<223> OTHER INFORMATION: p smallsyn vector

<400> SEQUENCE: 25

```
atcgatgttg acattgatta ttgactagtt attaatagta atcaattacg gggtcattag    60
ttcatagccc atatatggag ttccgcgtta cataacttac ggtaaatggc ccgcctggct   120
gaccgcccaa cgacccccgc ccattgacgt caataatgac gtatgttccc atagtaacgc   180
caatagggac tttccattga cgtcaatggg tggagtattt acggtaaact gcccacttgg   240
cagtacatca agtgtatcat atgccaagta cgccccctat tgacgtcaat gacggtaaat   300
ggcccgcctg gcattatgcc cagtacatga ccttatggga ctttcctact tggcagtaca   360
tctacgtatt agtcatcgct attaccatgg tgatgcggtt ttggcagtac atcaatgggc   420
gtggatagcg gtttgactca cggggatttc caagtctcca ccccattgac gtcaatggga   480
gtttgttttg gcaccaaaat caacgggact ttccaaaatg tcgtaacaac tccgccccat   540
tgacgcaaat gggcggtagg cgtgtacggt gggaggtcta taagcagag ctctctggc    600
taactagaga acccactgct tactggctta tctaaattaa tacgactcac tatagggaga   660
cccaagctgt taagcttggt agatatcagg gatccactca gctgatcagc ctccagttta   720
aacctgtgcc ttctagttgc cagccatctg ttgtttgccc ctcccccgtg ccttccttga   780
ccctggaagg tgccactccc actgtccttt cctaataaaa tgaggaaatt gcatcgcatt   840
gtctgagtag gtgtcattct attctggggg gtggggtggg caggacagc aaggggagg    900
attgggaaga caatagcagg catgctgggg atgcggtggg ctctatggcc cgggtagtga   960
attcatgtga gcaaaaggcc agcaaaaggc caggaaccgt aaaaaggccg cgttgctggc  1020
gttttttccat aggctccgcc cccctgacga gcatcacaaa atcgacgct caagtcagag  1080
gtggcgaaac ccgacaggac tataaagata ccaggcgttt ccccctggaa gctccctcgt  1140
gcgctctcct gttccgaccc tgccgcttac cggatacctg tccgcctttc tcccttcggg  1200
aagcgtggcg ctttctcata gctcacgctg taggtatctc agttcggtgt aggtcgttcg  1260
```

-continued

```
ctccaagctg ggctgtgtgc acgaaccccc cgttcagccc gaccgctgcg ccttatccgg      1320
taactatcgt cttgagtcca acccggtaag cacgacttta tcgccactgg cagcagccac      1380
tggtaacagg attagcagag cgaggtatgt aggcggtgct acagagttct tgaagtggtg      1440
gcctaactac ggctacacta aaggacagta tttggtatc tgcgctctgc tgaagccagt       1500
taccttcgga aaagagttg gtagctcttg atccggcaaa caaaccaccg ctggtagcgg       1560
tggttttttt gtttgcaagc agcagattac gcgcagaaaa aaggatctc aagaagatcc       1620 tttgatcttt tctacgggag atctgtctga ctctcagtgg aaccaaaact catgttaagg     1680
gattttggtc atgagattat caaaaaggat cttcacctag atccttttaa attaaaaatg     1740
aagttttaaa tcaatctaaa gtatatatga gtaaacttgg tctgacaggt taacttacca     1800
atgcttaatc aatgaggcac caatctctgc aatctgccta tttctctcat ccatggttgc     1860
ctgactgcct gtggtgtaga taactacaat cctggagggc ttaccatctg gccccagtgc    1920
tgcaatgata cctctagacc ctctctcacc tgctccagat ttatctgcaa tgaaccagcc    1980
agctggaagg gcagacctca gaagtggtcc tgcaacttta tctgcctcca tccagtctat    2040
taattgttgt ctggaagcta gagtaagcag ttcaccagtt aatagtttcc tcaaggttgt    2100
tgccattgct acaggcatgg tggtgtccct ctcatcattt ggtatggctt cattcagctc    2160
tggttcccat ctatcaagcc tagttacatg atcacccatg ttgtgcaaaa aagcagtcaa    2220
ctcctttggt cctccaatgg ttgtcaaaag taagttggca gcagtgttat cactcatggt    2280
tatggcagca ctgcataatt ctcttactgt catgccatct gtaagatgct tttctgtgac    2340
tggactgtac tcaaccaagt cattctgaga atagtgtatt cttctaccca gttgctcttg    2400
cccagcatca attctggata atactgcacc acatagcaga actttaaagg tgctcatcat    2460
tggaaatctt tcttctggtc taaaactctc aaggatctta ccagagttga gatccagttc    2520
aatgtaaccc actcttgcac ccaactgatc ttcagcatct tttactttca ccagggtttc   2580
tgggtgagca aaaacaggaa ggcaaaaggc agcaaaaaag ggaataaggg caactctgaa    2640
atgttgaata ctcatagtac tactcttcct ttttcaatat tattgaagca tttatcaggg   2700
ttattgtctc atgagcggat acatatttga atgtatttag aaaaataaac aaataggggt   2760
atgcattcag ctcacatttc cctgaaaagt gccacctgaa attgactgat agggagttct   2820
cccaatcccc tatggtgcac tctcagtaca atctgctctg atgcctcata gttaagccag    2880
tatctgctcc ctgcttgtgt gttggaggtc actgagtagt gggctagcaa aatttaagct   2940
acaacaaggc aaggcttgac ctacaattgc atgaagaatc tgcttagggt taggcctttt    3000
gcactgcttg gagatgtact ggccagatat acta                                3034
```

<210> SEQ ID NO 26
<211> LENGTH: 669
<212> TYPE: DNA
<213> ORGANISM: Artificial sequence
<220> FEATURE:
        <221) CDS
<222> LOCATION: (1)..(696)
<223> OTHER INFORMATION: p24 delta CpG gene (HIV-1 plasmid p24 (capsid
        protein) gene with depleted CpG dinucleotides)

<400> SEQUENCE: 26

```
atg gtg cac cag gcc atc agc ccc agg acc ctg aat gcc tgg gtg aag      48
Met Val His Gln Ala Ile Ser Pro Arg Thr Leu Asn Ala Trp Val Lys
 1               5                  10                  15 gtg gtg gag gag aag gcc ttc agc cct gag gtg atc ccc atg ttc tct     96
Val Val Glu Glu Lys Ala Phe Ser Pro Glu Val Ile Pro Met Phe Ser
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| gcc | ctg | tct | gag | ggg | gcc | acc | ccc | cag | gac | ctg | aac | acc | atg | ctg | aac | 144 |
| Ala | Leu | Ser | Glu | Gly | Ala | Thr | Pro | Gln | Asp | Leu | Asn | Thr | Met | Leu | Asn |  |
|  |  | 35 |  |  |  |  | 40 |  |  |  |  | 45 |  |  |  |  |
| aca | gtg | ggg | ggc | cac | cag | gct | gcc | atg | cag | atg | ctg | aag | gaa | acc | atc | 192 |
| Thr | Val | Gly | Gly | His | Gln | Ala | Ala | Met | Gln | Met | Leu | Lys | Glu | Thr | Ile |  |
|  | 50 |  |  |  |  | 55 |  |  |  |  | 60 |  |  |  |  |  |
| aat | gag | gag | gct | gct | gag | tgg | gac | aga | gtg | cac | cct | gtg | cat | gct | ggc | 240 |
| Asn | Glu | Glu | Ala | Ala | Glu | Trp | Asp | Arg | Val | His | Pro | Val | His | Ala | Gly |  |
| 65 |  |  |  |  | 70 |  |  |  |  | 75 |  |  |  |  | 80 |  |
| ccc | att | gcc | cct | ggc | cag | atg | agg | gag | ccc | agg | ggc | tct | gac | att | gct | 288 |
| Pro | Ile | Ala | Pro | Gly | Gln | Met | Arg | Glu | Pro | Arg | Gly | Ser | Asp | Ile | Ala |  |
|  |  |  |  | 85 |  |  |  |  | 90 |  |  |  |  | 95 |  |  |
| ggc | acc | acc | tcc | acc | ctg | cag | gag | cag | att | ggc | tgg | atg | acc | aac | aac | 336 |
| Gly | Thr | Thr | Ser | Thr | Leu | Gln | Glu | Gln | Ile | Gly | Trp | Met | Thr | Asn | Asn |  |
|  |  |  | 100 |  |  |  |  | 105 |  |  |  |  | 110 |  |  |  |
| ccc | ccc | atc | cct | gtg | ggg | gag | atc | tac | aag | aga | tgg | atc | atc | ctg | ggc | 384 |
| Pro | Pro | Ile | Pro | Val | Gly | Glu | Ile | Tyr | Lys | Arg | Trp | Ile | Ile | Leu | Gly |  |
|  |  | 115 |  |  |  |  | 120 |  |  |  |  | 125 |  |  |  |  |
| ctg | aac | aag | att | gtg | agg | atg | tac | agc | ccc | acc | tcc | atc | ctg | gac | atc | 432 |
| Leu | Asn | Lys | Ile | Val | Arg | Met | Tyr | Ser | Pro | Thr | Ser | Ile | Leu | Asp | Ile |  |
| 130 |  |  |  |  | 135 |  |  |  |  | 140 |  |  |  |  |  |  |
| agg | cag | ggc | ccc | aag | gag | ccc | ttc | agg | gac | tat | gtg | gac | agg | ttc | tac | 480 |
| Arg | Gln | Gly | Pro | Lys | Glu | Pro | Phe | Arg | Asp | Tyr | Val | Asp | Arg | Phe | Tyr |  |
| 145 |  |  |  |  | 150 |  |  |  |  | 155 |  |  |  |  | 160 |  |
| aag | acc | ctg | agg | gct | gag | cag | gcc | agc | cag | gag | gtg | aag | aac | tgg | atg | 528 |
| Lys | Thr | Leu | Arg | Ala | Glu | Gln | Ala | Ser | Gln | Glu | Val | Lys | Asn | Trp | Met |  |
|  |  |  |  | 165 |  |  |  |  | 170 |  |  |  |  | 175 |  |  |
| aca | gag | acc | ctg | ctg | gtg | cag | aat | gcc | aac | cct | gac | tgc | aag | acc | atc | 576 |
| Thr | Glu | Thr | Leu | Leu | Val | Gln | Asn | Ala | Asn | Pro | Asp | Cys | Lys | Thr | Ile |  |
|  |  |  | 180 |  |  |  |  | 185 |  |  |  |  | 190 |  |  |  |
| ctg | aag | gcc | ctg | ggc | cca | gct | gcc | acc | ctg | gag | gag | atg | atg | aca | gcc | 624 |
| Leu | Lys | Ala | Leu | Gly | Pro | Ala | Ala | Thr | Leu | Glu | Glu | Met | Met | Thr | Ala |  |
|  |  | 195 |  |  |  |  | 200 |  |  |  |  | 205 |  |  |  |  |
| tgc | cag | ggg | gtg | gga | ggc | cct | ggc | cac | aag | gcc | agg | gtg | ctg | taa |  | 669 |
| Cys | Gln | Gly | Val | Gly | Gly | Pro | Gly | His | Lys | Ala | Arg | Val | Leu |  |  |  |
| 210 |  |  |  |  | 215 |  |  |  |  | 220 |  |  |  |  |  |  |

<210> SEQ ID NO 27
<211> LENGTH: 222
<212> TYPE: PRT
<213> ORGANISM: Artificial sequence
<220> FEATURE:
<223> OTHER INFORMATION: p24 delta CpG gene (HIV-1 plasmid p24 (capsid protein) gene with depleted CpG dinucleotides)

<400> SEQUENCE: 27

Met Val His Gln Ala Ile Ser Pro Arg Thr Leu Asn Ala Trp Val Lys
1               5                   10                  15

Val Val Glu Glu Lys Ala Phe Ser Pro Glu Val Ile Pro Met Phe Ser
                20                  25                  30

Ala Leu Ser Glu Gly Ala Thr Pro Gln Asp Leu Asn Thr Met Leu Asn
            35                  40                  45

Thr Val Gly Gly His Gln Ala Ala Met Gln Met Leu Lys Glu Thr Ile
        50                  55                  60

Asn Glu Glu Ala Ala Glu Trp Asp Arg Val His Pro Val His Ala Gly
65                  70                  75                  80

Pro Ile Ala Pro Gly Gln Met Arg Glu Pro Arg Gly Ser Asp Ile Ala
                85                  90                  95

```
Gly Thr Thr Ser Thr Leu Gln Glu Gln Ile Gly Trp Met Thr Asn Asn
            100                 105                 110

Pro Pro Ile Pro Val Gly Glu Ile Tyr Lys Arg Trp Ile Ile Leu Gly
        115                 120                 125

Leu Asn Lys Ile Val Arg Met Tyr Ser Pro Thr Ser Ile Leu Asp Ile
    130                 135                 140

Arg Gln Gly Pro Lys Glu Pro Phe Arg Asp Tyr Val Asp Arg Phe Tyr
145                 150                 155                 160

Lys Thr Leu Arg Ala Glu Gln Ala Ser Gln Glu Val Lys Asn Trp Met
                165                 170                 175

Thr Glu Thr Leu Leu Val Gln Asn Ala Asn Pro Asp Cys Lys Thr Ile
            180                 185                 190

Leu Lys Ala Leu Gly Pro Ala Ala Thr Leu Glu Glu Met Met Thr Ala
        195                 200                 205

Cys Gln Gly Val Gly Gly Pro Gly His Lys Ala Arg Val Leu
210                 215                 220
```

<210> SEQ ID NO 28
<211> LENGTH: 34
<212> TYPE: DNA
<213> ORGANISM: Artificial sequence
<220> FEATURE:
<223> OTHER INFORMATION: Primer huGFP-1

<400> SEQUENCE: 28
caataagctt gccaccatgg tgagcaaggg cgag                              34

<210> SEQ ID NO 29
<211> LENGTH: 29
<212> TYPE: DNA
<213> ORGANISM: Artificial sequence
<220> FEATURE:
<223> OTHER INFORMATION: Primer huGFP-2

<400> SEQUENCE: 29
agtaggatcc tattacttgt acagctcgt                                   29

<210> SEQ ID NO 30
<211> LENGTH: 20
<212> TYPE: DNA
<213> ORGANISM: Artificial sequence
<220> FEATURE:
<223> OTHER INFORMATION: Primer RT-oligo1

<400> SEQUENCE: 30
ccctgaagtt catctgcacc                                             20

<210> SEQ ID NO 31
<211> LENGTH: 22
<212> TYPE: DNA
<213> ORGANISM: Artificial sequence
<220> FEATURE:
<223> OTHER INFORMATION: Primer oligo2

<400> SEQUENCE: 31
gatcttgaag ttcaccttga tg                                          22

<210> SEQ ID NO 32
<211> LENGTH: 34
<212> TYPE: DNA
<213> ORGANISM: Artificial sequence
<220> FEATURE:
<223> OTHER INFORMATION: Primer mamip-1

```
<400> SEQUENCE: 32
caggtaccaa gcttatgaag gtctccacca ctgc                                    34

<210> SEQ ID NO 33
<211> LENGTH: 43
<212> TYPE: DNA
<213> ORGANISM: Artificial sequence
<220> FEATURE:
<223> OTHER INFORMATION: Primer mamip-2

<400> SEQUENCE: 33
cagagctcga gtcatgaaga ctaggcattc agttccaggt cag                          43

<210> SEQ ID NO 34
<211> LENGTH: 33
<212> TYPE: DNA
<213> ORGANISM: Artificial sequence
<220> FEATURE:
<223> OTHER INFORMATION: Primer hugm-1

<400> SEQUENCE: 34
caggtaccaa gcttatgtgg ctgcagagcc tgc                                     33

<210> SEQ ID NO 35
<211> LENGTH: 43
<212> TYPE: DNA
<213> ORGANISM: Artificial sequence
<220> FEATURE:
<223> OTHER INFORMATION: Primer hugm-2

<400> SEQUENCE: 35
cagagctcga gtcatgaaga ctactcctgg actggctccc agc                          43

<210> SEQ ID NO 36
<211> LENGTH: 33
<212> TYPE: DNA
<213> ORGANISM: Artificial sequence
<220> FEATURE:
<223> OTHER INFORMATION: Primer humip-1

<400> SEQUENCE: 36
cagtaccaag cttatgcagg tctccactgc tgc                                     33

<210> SEQ ID NO 37
<211> LENGTH: 45
<212> TYPE: DNA
<213> ORGANISM: Artificial sequence
<220> FEATURE:
<223> OTHER INFORMATION: Primer humip-2

<400> SEQUENCE: 37
cagagctcga gtcatgaaga ctaggcactc agctccaggt cactg                        45

<210> SEQ ID NO 38
<211> LENGTH: 43
<212> TYPE: DNA
<213> ORGANISM: Artificial sequence
<220> FEATURE:
<223> OTHER INFORMATION: Primer  p24-1

<400> SEQUENCE: 38
actaggtacc atctaagctt atgcccatcg tgcagaacat cca                          43

<210> SEQ ID NO 39
```

<211> LENGTH: 45
<212> TYPE: DNA
<213> ORGANISM: Artificial sequence
<220> FEATURE:
<223> OTHER INFORMATION: Primer p24-2

<400> SEQUENCE: 39
tcaagagctc gactggatcc tattacagca ccctggcctt gtggc            45

<210> SEQ ID NO 40
<211> LENGTH: 41
<212> TYPE: DNA
<213> ORGANISM: Artificial sequence
<220> FEATURE:
<223> OTHER INFORMATION: Primer CMV-1

<400> SEQUENCE: 40
caaaggtacc gttaatcgat gttgacattg attattgact a                41

<210> SEQ ID NO 41
<211> LENGTH: 24
<212> TYPE: DNA
<213> ORGANISM: Artificial sequence
<220> FEATURE:
<223> OTHER INFORMATION: Primer CMV-2

<400> SEQUENCE: 41
gaatgagctc tgcttatata gacc                                   24

<210> SEQ ID NO 42
<211> LENGTH: 35
<212> TYPE: DNA
<213> ORGANISM: Artificial sequence
<220> FEATURE:
<223> OTHER INFORMATION: Primer ori-1

<400> SEQUENCE: 42
gtcacccggg tagtgaattc atgtgagcaa aaggc                       35

<210> SEQ ID NO 43
<211> LENGTH: 35
<212> TYPE: DNA
<213> ORGANISM: Artificial sequence
<220> FEATURE:
<223> OTHER INFORMATION: Primer ori-2

<400> SEQUENCE: 43
gatcttttct acgggagatc tgtcaatcga tagct                       35

<210> SEQ ID NO 44
<211> LENGTH: 42
<212> TYPE: DNA
<213> ORGANISM: Artificial sequence
<220> FEATURE:
<223> OTHER INFORMATION: Primer pa-1

<400> SEQUENCE: 44
gttagagctc cagtgtttaa acctgtgcct tctagttgcc ag               42

<210> SEQ ID NO 45
<211> LENGTH: 39
<212> TYPE: DNA
<213> ORGANISM: Artificial sequence
<220> FEATURE:
<223> OTHER INFORMATION: Primer pa-2

<400> SEQUENCE: 45
caaacctacc gatacccggg ccatagagcc caccgcatc					39

<210> SEQ ID NO 46
<211> LENGTH: 42
<212> TYPE: DNA
<213> ORGANISM: Artificial sequence
<220> FEATURE:
<223> OTHER INFORMATION: Primer ref-del-1

<400> SEQUENCE: 46
tcagatgcat ccgtacgtta acatgtgagc aaaaggccag ca					42

<210> SEQ ID NO 47
<211> LENGTH: 33
<212> TYPE: DNA
<213> ORGANISM: Artificial sequence
<220> FEATURE:
<223> OTHER INFORMATION: Primer ref-del-2

<400> SEQUENCE: 47
agtcatgcat ccatagagcc caccgcatcc cca					33

<210> SEQ ID NO 48
<211> LENGTH: 33
<212> TYPE: DNA
<213> ORGANISM: Artificial sequence
<220> FEATURE:
<223> OTHER INFORMATION: Primer 5'-3' huil-1

<400> SEQUENCE: 48
caggtaccaa gcttatgaga atttcgaaac cac					33

<210> SEQ ID NO 49
<211> LENGTH: 45
<212> TYPE: DNA
<213> ORGANISM: Artificial sequence
<220> FEATURE:
<223> OTHER INFORMATION: Primer 5'-3 huil-2

<400> SEQUENCE: 49
cagagctcga gtcatgaaga ctaagaagtg ttgatgaaca tttgg					45

<210> SEQ ID NO 50
<211> LENGTH: 34
<212> TYPE: DNA
<213> ORGANISM: Artificial sequence
<220> FEATURE:
<223> OTHER INFORMATION: Primer 5'-3' magm-1

<400> SEQUENCE: 50
caggtaccaa gcttatggcc cacgagagaa aggc					34

<210> SEQ ID NO 51
<211> LENGTH: 43
<212> TYPE: DNA
<213> ORGANISM: Artificial sequence
<220> FEATURE:
<223> OTHER INFORMATION: Primer 5'-3' magm-2

<400> SEQUENCE: 51
cagagctcga gtcatgaaga ctattttggg cctggttttt tgc					43

<210> SEQ ID NO 52
<211> LENGTH: 489
<212> TYPE: DNA

<213> ORGANISM: Artificial sequence
<220> FEATURE:
<221> NAME/KEY: CDS
<222> LOCATION: (1)..(489)
<223> OTHER INFORMATION: Synthetic gene human IL-15-21CpG

<400> SEQUENCE: 52

```
atg cgg atc agc aag ccc cac ctg agg agc atc agc atc cag tgc tac     48
Met Arg Ile Ser Lys Pro His Leu Arg Ser Ile Ser Ile Gln Cys Tyr
 1               5                  10                  15 ctg tgc ctg ctg ctg aac agc cac ttc ctg aca gag gcc ggc atc cac     96
Leu Cys Leu Leu Leu Asn Ser His Phe Leu Thr Glu Ala Gly Ile His
             20                  25                  30 gtg ttt atc ctg ggc tgc ttc tct gcc ggc ctg cct aag aca gag gcc    144
Val Phe Ile Leu Gly Cys Phe Ser Ala Gly Leu Pro Lys Thr Glu Ala
         35                  40                  45 aac tgg gtg aac gtg atc agc gac ctg aag aag atc gag gac ctg atc    192
Asn Trp Val Asn Val Ile Ser Asp Leu Lys Lys Ile Glu Asp Leu Ile
     50                  55                  60 cag agc atg cac atc gac gcc acc ctg tac aca gag agc gac gtg cac    240
Gln Ser Met His Ile Asp Ala Thr Leu Tyr Thr Glu Ser Asp Val His
 65                  70                  75                  80 cct agc tgt aag gtg acc gcc atg aag tgc ttc ctg ctg gag ctg cag    288
Pro Ser Cys Lys Val Thr Ala Met Lys Cys Phe Leu Leu Glu Leu Gln
                 85                  90                  95 gtg atc agc ctg gag agc ggc gat gcc agc atc cac gac acc gtg gag    336
Val Ile Ser Leu Glu Ser Gly Asp Ala Ser Ile His Asp Thr Val Glu
            100                 105                 110 aac ctg atc atc ctg gcc aac aac agc ctg agc agc aac ggc aat gtg    384
Asn Leu Ile Ile Leu Ala Asn Asn Ser Leu Ser Ser Asn Gly Asn Val
        115                 120                 125 acc gag agc ggc tgc aag gag tgt gag gag ctg gag gag aag aac atc    432
Thr Glu Ser Gly Cys Lys Glu Cys Glu Glu Leu Glu Glu Lys Asn Ile
    130                 135                 140 aag gag ttc ctg cag agc ttc gtg cac atc gtg cag atg ttc atc aac    480
Lys Glu Phe Leu Gln Ser Phe Val His Ile Val Gln Met Phe Ile Asn
145                 150                 155                 160 acc agc tag                                                        489
Thr Ser
```

<210> SEQ ID NO 53
<211> LENGTH: 162
<212> TYPE: PRT
<213> ORGANISM: Artificial sequence
<220> FEATURE:
<223> OTHER INFORMATION: human IL-15-21CpG

<400> SEQUENCE: 53

```
Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95
```

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 54
<211> LENGTH: 426
<212> TYPE: DNA
<213> ORGANISM: Artificial sequence
<220> FEATURE:
<221> NAME/KEY: CDS
<222> LOCATION: (1)..(426)
<223> OTHER INFORMATION: Synthetic gene for murine GM-CSF-62CpG

<400> SEQUENCE: 54

```
atg tgg ctg cag aac ctg ctg ttc ctc ggc atc gtc gtg tac tcg ctg      48
Met Trp Leu Gln Asn Leu Leu Phe Leu Gly Ile Val Val Tyr Ser Leu
 1               5                  10                  15 agc gcg ccg acg cgc tcg ccg atc acc gtg acg cgg ccg tgg aag cac      96
Ser Ala Pro Thr Arg Ser Pro Ile Thr Val Thr Arg Pro Trp Lys His
                20                  25                  30 gtc gag gcg atc aag gag gcg ctg aac ctg ctc gac gac atg ccc gtg     144
Val Glu Ala Ile Lys Glu Ala Leu Asn Leu Leu Asp Asp Met Pro Val
            35                  40                  45 acg ctg aac gag gag gtc gag gtc gtg tcg aac gag ttc tcg ttc aag     192
Thr Leu Asn Glu Glu Val Glu Val Val Ser Asn Glu Phe Ser Phe Lys
        50                  55                  60 aag ctg acg tgc gtg cag acg cgg ctg aag atc ttc gag cag ggc ctg     240
Lys Leu Thr Cys Val Gln Thr Arg Leu Lys Ile Phe Glu Gln Gly Leu
65                  70                  75                  80 cgc ggc aac ttc acg aag ctg aag ggc gcg ctg aac atg acc gcg tcg     288
Arg Gly Asn Phe Thr Lys Leu Lys Gly Ala Leu Asn Met Thr Ala Ser
                85                  90                  95 tac tac cag acg tac tgc ccg ccg acg ccc gag acc gat tgc gag acg     336
Tyr Tyr Gln Thr Tyr Cys Pro Pro Thr Pro Glu Thr Asp Cys Glu Thr
            100                 105                 110 cag gtg acg acg tac gcc gac ttc atc gac tcg ctg aag acg ttc ctg     384
Gln Val Thr Thr Tyr Ala Asp Phe Ile Asp Ser Leu Lys Thr Phe Leu
        115                 120                 125 acc gac atc ccg ttc gag tgc aag aag ccc ggc cag aag tag             426
Thr Asp Ile Pro Phe Glu Cys Lys Lys Pro Gly Gln Lys
130                 135                 140
```

<210> SEQ ID NO 55
<211> LENGTH: 141
<212> TYPE: PRT
<213> ORGANISM: Artificial sequence
<220> FEATURE:
<223> OTHER INFORMATION: murine GM-CSF-62CpG

<400> SEQUENCE: 55

Met Trp Leu Gln Asn Leu Leu Phe Leu Gly Ile Val Val Tyr Ser Leu
 1               5                  10                  15

Ser Ala Pro Thr Arg Ser Pro Ile Thr Val Thr Arg Pro Trp Lys His
                20                  25                  30

Val Glu Ala Ile Lys Glu Ala Leu Asn Leu Leu Asp Asp Met Pro Val

```
                35                  40                  45

Thr Leu Asn Glu Glu Val Glu Val Val Ser Asn Glu Phe Ser Phe Lys
         50                  55                  60

Lys Leu Thr Cys Val Gln Thr Arg Leu Lys Ile Phe Glu Gln Gly Leu
 65                  70                  75                  80

Arg Gly Asn Phe Thr Lys Leu Lys Gly Ala Leu Asn Met Thr Ala Ser
                 85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
130                 135                 140

<210> SEQ ID NO 56
<211> LENGTH: 489
<212> TYPE: DNA
<213> ORGANISM: Homo sapiens
<220> FEATURE:
<221> NAME/KEY: CDS
<222> LOCATION: (1)..(489)
<223> OTHER INFORMATION: human IL-15 wild-type (3CpG)

<400> SEQUENCE: 56 atg aga att tcg aaa cca cat ttg aga agt att tcc atc cag tgc tac       48
Met Arg Ile Ser Lys Pro His Leu Arg Ser Ile Ser Ile Gln Cys Tyr
  1               5                  10                  15 ttg tgt tta ctt cta aac agt cat ttt cta act gaa gct ggc att cat       96
Leu Cys Leu Leu Leu Asn Ser His Phe Leu Thr Glu Ala Gly Ile His
             20                  25                  30 gtc ttc att ttg ggc tgt ttc agt gca ggg ctt cct aaa aca gaa gcc      144
Val Phe Ile Leu Gly Cys Phe Ser Ala Gly Leu Pro Lys Thr Glu Ala
         35                  40                  45 aac tgg gtg aat gta ata agt gat ttg aaa aaa att gaa gat ctt att      192
Asn Trp Val Asn Val Ile Ser Asp Leu Lys Lys Ile Glu Asp Leu Ile
 50                  55                  60 caa tct atg cat att gat gct act tta tat acg gaa agt gat gtt cac      240
Gln Ser Met His Ile Asp Ala Thr Leu Tyr Thr Glu Ser Asp Val His
 65                  70                  75                  80 ccc agt tgc aaa gta aca gca atg aag tgc ttt ctc ttg gag tta caa      288
Pro Ser Cys Lys Val Thr Ala Met Lys Cys Phe Leu Leu Glu Leu Gln
                 85                  90                  95 gtt att tca ctt gag tcc gga gat gca agt att cat gat aca gta gaa      336
Val Ile Ser Leu Glu Ser Gly Asp Ala Ser Ile His Asp Thr Val Glu
            100                 105                 110 aat ctg atc atc cta gca aac aac agt ttg tct tct aat ggg aat gta      384
Asn Leu Ile Ile Leu Ala Asn Asn Ser Leu Ser Ser Asn Gly Asn Val
        115                 120                 125 aca gaa tct gga tgc aaa gaa tgt gag gaa ctg gag gaa aaa aat att      432
Thr Glu Ser Gly Cys Lys Glu Cys Glu Glu Leu Glu Glu Lys Asn Ile
    130                 135                 140 aaa gaa ttt ttg cag agt ttt gta cat att gtc caa atg ttc atc aac      480
Lys Glu Phe Leu Gln Ser Phe Val His Ile Val Gln Met Phe Ile Asn
145                 150                 155                 160 act tct tag                                                          489
Thr Ser

<210> SEQ ID NO 57
<211> LENGTH: 162
<212> TYPE: PRT
```

<213> ORGANISM: Homo sapiens
<220> FEATURE:
<223> OTHER INFORMATION: human IL-15 wild-type (3CpG)

<400> SEQUENCE: 57

```
Met Arg Ile Ser Lys Pro His Leu Arg Ser Ile Ser Ile Gln Cys Tyr
  1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 58
<211> LENGTH: 426
<212> TYPE: DNA
<213> ORGANISM: Mus musculus
<220> FEATURE:
<221> NAME/KEY: CDS
<222> LOCATION: (1)..(426)
<223> OTHER INFORMATION: murine GM-CSF wild-type (11CpG)

<400> SEQUENCE: 58

```
atg tgg ctg cag aat tta ctt ttc ctg ggc att gtg gtc tac agc ctc      48
Met Trp Leu Gln Asn Leu Leu Phe Leu Gly Ile Val Val Tyr Ser Leu
  1               5                  10                  15 tca gca ccc acc cgc tca ccc atc act gtc acc cgg cct tgg aag cat      96
Ser Ala Pro Thr Arg Ser Pro Ile Thr Val Thr Arg Pro Trp Lys His
             20                  25                  30 gta gag gcc atc aaa gaa gcc ctg aac ctc ctg gat gac atg cct gtc     144
Val Glu Ala Ile Lys Glu Ala Leu Asn Leu Leu Asp Asp Met Pro Val
         35                  40                  45 aca ttg aat gaa gag gta gaa gtc gtc tct aac gag ttc tcc ttc aag     192
Thr Leu Asn Glu Glu Val Glu Val Val Ser Asn Glu Phe Ser Phe Lys
     50                  55                  60 aag cta aca tgt gtg cag acc cgc ctg aag ata ttc gag cag ggt cta     240
Lys Leu Thr Cys Val Gln Thr Arg Leu Lys Ile Phe Glu Gln Gly Leu
 65                  70                  75                  80 cgg ggc aat ttc acc aaa ctc aag ggc gcc ttg aac atg aca gcc agc     288
Arg Gly Asn Phe Thr Lys Leu Lys Gly Ala Leu Asn Met Thr Ala Ser
                 85                  90                  95 tac tac cag aca tac tgc ccc cca act ccg gaa acg gac tgt gaa aca     336
Tyr Tyr Gln Thr Tyr Cys Pro Pro Thr Pro Glu Thr Asp Cys Glu Thr
            100                 105                 110 caa gtt acc acc tat gcg gat ttc ata gac agc ctt aaa acc ttt ctg     384
```

```
Gln Val Thr Thr Tyr Ala Asp Phe Ile Asp Ser Leu Lys Thr Phe Leu
        115                 120                 125 act gat atc ccc ttt gaa tgc aaa aaa cca ggc caa aaa tag              426
Thr Asp Ile Pro Phe Glu Cys Lys Lys Pro Gly Gln Lys
        130                 135                 140

<210> SEQ ID NO 59
<211> LENGTH: 141
<212> TYPE: PRT
<213> ORGANISM: Mus musculus
<220> FEATURE:
<223> OTHER INFORMATION: murine GM-CSF-wildtyp (11 CpG)

<400> SEQUENCE: 59

Met Trp Leu Gln Asn Leu Leu Phe Leu Gly Ile Val Val Tyr Ser Leu
 1               5                  10                  15

Ser Ala Pro Thr Arg Ser Pro Ile Thr Val Thr Arg Pro Trp Lys His
                20                  25                  30

Val Glu Ala Ile Lys Glu Ala Leu Asn Leu Leu Asp Asp Met Pro Val
            35                  40                  45

Thr Leu Asn Glu Glu Val Glu Val Val Ser Asn Glu Phe Ser Phe Lys
        50                  55                  60

Lys Leu Thr Cys Val Gln Thr Arg Leu Lys Ile Phe Glu Gln Gly Leu
 65                 70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
                100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
        130                 135                 140
```

METHOD FOR MODULATING GENE EXPRESSION BY MODIFYING THE CPG CONTENT

This is a §371 of PCT/EP2005/008423 filed Aug. 3, 2005, which claims priority from German Patent Application No. 10 2004 037 611.5 filed Aug. 3, 2004 and German Patent Application No. 10 2004 037 652.2 filed Aug. 3, 2004.

The present invention relates to modified polynucleotides that are derived from naturally occurring and synthetic genes or other coding sequences, and that have a reduced or increased number of CpG dinucleotides in the coding region compared to the original sequence. These polynucleotides may be used in order to investigate, increase or reduce the gene expression and, in a special case, to improve the production of biomolecules, the efficiency of DNA vaccines or gene therapy constructs, as well as the quality of transgenic animals or plants.

BACKGROUND OF THE INVENTION

The provision of biomolecules in the form of peptides, proteins or RNA molecules is an important component in the biotechnology and pharmaceutical sector. Proteins and RNAs produced by recombinant technology or expressed in vivo are used to investigate basic mechanisms and relationships, as well as in the production of biotechnology reagents, in the production of transgenic animals or plants, or for medical applications in the development of treatments and vaccines. Depending on the application, the level of expression of corresponding molecules should be able to be regulated.

In most cases increases above the standard production levels are desired. Each expression system or vector construct has limitations, which determine the actual production output. The present invention relates to methods and applications that are able to modulate the level of expression of arbitrary genes in eukaryotic cells. In particular the method is suitable for modulating arbitrary genes so that the achievable gene expression is above the level that can be achieved with hitherto known methods for increasing the expression.

PRIOR ART

CpG dinucleotides occupy an important position in the genome of eukaryotes. They are not randomly distributed like other dinucleotides, but instead are under-represented over wide stretches of the genome. In addition CpG dinucleotides in these regions are generally methylated.

An exception to this are regions that have a very much higher density of CpG dinucleotides, and which on account of these properties are termed CpG islands. A characteristic property of these CpG islands and a further difference with respect to the CpG dinucleotides is the fact that the CpG dinucleotides in the islands are as a rule not present in methylated form.

The under-representation of CpG dinucleotides is explained by a chemical modification of the corresponding nucleotides. In the genome of vertebrates about 60-90% of the cytosines in CpG dinucleotides are present in methylated form and these methylated cytosines are often modified by deamination to thymines (Shen et al., 1994).

As a result of this process the frequency of cytosines and guanosines is below the expected statistical distribution, and is about 40%, and the proportion of CpG dinucleotides is even only about 20% of the frequency to be expected (Bird, 1980; Sved et al., 1990; Takai et al., 2002).

CpG islands form an exception to this unusual distribution of CpG dinucleotides (Antequera et al., 1993). CpG islands are mostly located in the vicinity of promoters, and may extend into the transcribed region or even lie within exons.

They are characterised by an approximately ten-times higher CpG frequency (ca. 60-70% C+G content) compared to average gene regions, and are characterised especially by the fact that as a rule they contain non-methylated CpGs (Wise et al., 1999). About 60% of all human genes, especially all housekeeping genes and approximately half of tissue-specific genes are associated with CpG islands (Antequera et al., 1993; Larsen et al., 1992). CpG islands have been described and defined inter alia in the publications by Gardiner-Garden M. & Frommer M (1997) J. Mol. Bio. 196, 261-282 and Takai D. & Jones P. A. (2002) PNAS 99, 3740-3745. Since various definitions exist in the prior art, for the purposes of the present invention a CpG island is defined as follows: a CpG island comprises a sequence of at least 500 successive base pairs with a CpG content of at least 55% and a quotient of (actual CpG/expected CpG) of at least 0.65, and it is associated with a promoter (overlapped wholly or partly by a promoter).

This unequal distribution and modification of CpG dinucleotides, i) under-represented and methylated on the one hand, and ii) concentrated and unmethylated in islands on the other hand, has an important control function in the regulation of the gene expression (illustrated diagrammatically in FIG. 1).

CpG dinucleotides are involved in the regulation of the gene expression in early developmental stages, in connection with cell differentiation, genetic imprinting and other procedures. A large number of studies has shown that in eukaryotes, the methylation of 5'CpG3' dinucleotides (mCpG) has a repressing effect on the gene expression in vertebrates and flowering plants (Hsieh, 1994; Kudo, 1998; Jones et al., 1998; Deng et al., 2001; Hisano et al., 2003 Li et al., 2004) (FIG. 1A).

Also, in tumour research there are numerous data that prove that, i) the switching off of the expression of certain genes, often suppressor genes, is caused by a hypermethylation of CpGs (Li et al., 2004; Kang et al., 2004; Ivanova et al., 2004; Wu et al., 2003), but also that, ii) the uncontrolled expression of other genes is associated with a hypomethylation (Akiyama et al., 2003; Yoshida et al., 2003).

The process of gene switching off by methylation is explained by a cascade of events which finally lead to a change of the chromatin structure, which creates a transcription-weak state. The methylation of 5'-CpG-3' dinucleotides within genes generates a potential binding site for protein complexes (primarily from the family of MeCP (methyl-CpG-binding proteins) and MBD (methyl-CpG binding domain protein) proteins), which bind methylated DNA sequences and at the same time associate with histone deacetylases (MBD-HDAC) and transcriptional redressor proteins (Jones et al., 1998; Nan et al., 1998; Hendrich et al., 1998). These complexes involve as a rule a restructuring of the chromatin, which leads to a switching off of the transcription activity (Wade et al., 1999). The methylation in promoter regions may also lead directly to a switching off of the gene expression, by preventing the binding of essential transcription factors due to the introduced methyl groups (Deng et al., 2001).

The above described deregulation of the expression in tumour cells is generally connected with an alteration of the methylation state in the above described CpG islands. In normal cells actively expressed genes are mostly associated with CpG islands, which are not, or are only slightly, methylated (FIG. 1B). The methylation of the CpG dinucleotides in these islands lead to a switching off of the expression of these genes (often tumour suppressor genes or cell cycle regulator genes) (FIG. 1C), and as a result leads to an uncontrolled multiplication of these cells. Conversely, genes that are inactive due to a methylation of the CpG dinucleotides in CpG islands are activated by a demethylation.

The aforedescribed demethylation in CpG islands leads, through an alteration of the chromatin structure, to a transcription-active state analogous to gene switching off in the case of a methylation. In addition to structural alterations there may also be an activation of the expression due to activator proteins. The human CpG-binding protein (hCGBP) is such a cellular activator protein. HCGBP binds specifically to non-methylated CpG dinucleotides in the region of promoters, where as a transactivator it leads to an increase in transcription (Voo et al., 2000).

Hitherto the knowledge that a methylation of the CpG sequences within a gene regulates the transcription downwards has been used to prevent the expression of a gene that is either over-expressed, or whose expression is undesired, by methylation (Choi et al., 2004; Yao et al., 2003) (cf. FIG. 1A).

A further application of this knowledge is the targeted elimination of such CpG dinucleotides in order to improve gene expression (Chevalier-Mariette et al., 2003). Due to an elimination a methylation and, associated therewith, a change of the chromatin structure to a transcription-inactive state, is likewise prevented (FIG. 1D). In this publication there is investigated the expression of a transgene with various CpG dinucleotide contents in operative coupling with a promoter that is located within a CpG island, in germ line cells and the embryos of transgenic mice formed therefrom. In this special case a transcriptional switching off of a reporter gene was prevented by the elimination of CpG dinucleotides (FIG. 1D transgene without CpG), as is otherwise to be expected by a de novo methylation of existing CpG dinucleotides during embryo development (FIG. 1D, transgene CpG high). A more detailed investigation of the mechanism in the publication by Chevalier-Mariette showed that the prevention of the gene expression is connected with a methylation of the intragenic CpG dinucleotides, as well as and especially with a subsequently occurring methylation of the promoter-associated CpG islands (FIG. 1D, transgene CpG high). For a reporter gene that did not have these intragenic CpG dinucleotides and that was not efficiently expressed, it was shown that the CpG island was not methylated (FIG. 1D, transgene without CpG). The authors therefore concluded that, for a lasting in vivo expression, the CpG dinucleotide content must be reduced in the immediate vicinity of the promoter and of the CpG island.

An increase in gene expression may similarly be achieved by the integration of complete CpG islands 5' of a promoter in corresponding vector constructs (WO 02081677) (cf. FIG. 1B). In the identification of hCGBP, CpG dinucleotides were likewise integrated into the corresponding promoter region of a reporter gene and an increase in reporter activity was found. In these transient cell culture tests however the hCGBP was likewise over-expressed and was therefore present in non-physiological raised concentrations (Voo, et al., 2000).

It is already known that the C/G content has an influence on the mRNA stability. Thus, for example, Duan and Antezana (2003) show that the expression of three different variants of a human gene in CHO cells consequently leads to differences in the mRNA concentration. In the first variant the human gene sequence had been altered so that the number of C/G dinucleotides was maximised. In a second variant on the other hand, the number of T/A dinucleotides had been maximised. The differences in the steady-state level, i.e. in the amount of mRNA, could be attributed experimentally to differences in the breakdown of the mRNA. On account of a stabilisation of the secondary structure with a raised C/G content, corresponding mRNAs were less strongly broken down than wild type, and correspondingly T/A-rich mRNAs were broken down to a much higher degree than wild type. An analysis was not carried out at the protein level, and also no increase in protein production due to an increase of the CpG dinucleotides was to be expected, since a stabilisation of the secondary structure of the mRNA negatively influences the translation.

Deml et al. disclose a sequence of the HIV-I Gag gene for codon-optimised expression in mammalian cells. A specific increase of CpG dinucleotides is not disclosed.

The object of the invention was to provide a method for the targeted modulation of the gene expression that at least partly avoids the disadvantages of the prior art.

This object is achieved by a method for the targeted modulation of the gene expression, comprising the following steps:
i. Provision of a target nucleic acid sequence to be expressed,
ii. Modification of the target nucleic acid sequence, in which the number of CpG dinucleotides present in the target nucleic acid sequence is raised using the degeneracy of the genetic code to increase the gene expression, or is lowered to reduce the gene expression,
iii. Cloning of the thereby modified target nucleic acid sequence with a modified number of the CpG dinucleotides in a suitable expression vector in operative coupling with a suitable transcription control sequence,
iv. Expression of the modified target nucleic acid sequence in a suitable expression system.

It was extremely surprisingly found that, when using the method of the present invention, exactly the opposite effect can be achieved than would have been expected according to a knowledge of the prior art. This means that, with the method of the present invention, by raising the number of CpG dinucleotides in a target nucleic acid sequence the expression of this target nucleic acid sequence can be raised, whereas by reducing the number of CpG dinucleotides in the target nucleic acid sequence its expression is prevented. The increase in the number of CpG dinucleotides in the reading frame should, according to the invention, not be equated to the introduction of a CpG island. The increase of the CpG dinucleotides in the reading frame differs by definition from a CpG island, due to i) a possible lower base number (<500) and ii) the absence of an overlapping with the promoter region.

The expression system may on the one hand be a cell, or on the other hand a cell-free system or in vitro system. A prokaryotic or eukaryotic expression system may be used, though a eukaryotic expression system is preferably employed. Suitable expression systems include e.g. bacterial cells, insect cells, e.g. Baculovirus expression systems, SF9 cells, Drosophila-Schneider cells, plant cells, yeasts, e.g. *Saccharomyces Cerevisiae, Pichia angusta, Pichia pastoris* and the like; as well as also algae, e.g. Chlamydomonas. Examples of possible plant expression systems include *Arabidopsis thaliana, Zea mays* (corn), *Nicotiana tobacco* (tobacco), *Oryza sativa* (rice), *Hordeum vulgare* (barley), *Glicine max* (soya), *Brassica* sp. (cabbage) and the like. Preferably vertebrate cells are used, in particular mammalian cells, especially human cells, in particular somatic cells and no germ line cells. Particularly preferably the expression system is a system or a cell with a low level of methylation, i.e. substantially no de novo methylation takes place. On the other hand it is also possible to use this method for the production of transgenic non-human organisms, in particular plants and animals.

The present invention thus relates in particular to a method for the targeted alteration of the level of expression of a transcript and/or for the targeted alteration of protein production, in particular in eukaryotic cells. The method is characterised by modifications of the reading frame of a DNA sequence to be transcribed.

The modifications relate to a variation of the proportion of CpG dinucleotides, which correlate with a change of the level of expression.

The technology of artificial gene synthesis enables any arbitrary nucleotide sequence chosen from these possibilities to be synthesised. By varying motifs within the coding region of a gene which correlate with the level of expression, the protein production can with this technology be modulated in a targeted manner by the choice of the corresponding nucleotide sequence. Within the scope of the present invention CpG dinucleotides were identified as such a motif having a direct influence on the level of expression.

It was surprisingly found that, in contrast to the generally accepted opinion, the introduction of CpG dinucleotides in the way and manner according to the invention leads to an increase of the gene expression instead of to a reduction of the expression. Conversely, the elimination of CpGs leads to a reduction of the gene expression.

The term "gene expression" within the context of the present invention includes both transcription as well as translation, and in particular this term is understood to include protein production.

These changes at the nucleic acid level are introduced within the scope of the present invention preferably by the production of an artificial gene by de novo gene synthesis, in which the amino acid sequence for which the corresponding gene codes preferably remains unchanged. De novo gene synthesis methods are known to the person skilled in the art in this field. The alteration of the CpG content is preferably carried out by silent mutations or by mutations that do not destroy the activity of the gene product. The modified target nucleic acid sequences may, as stated in the example, be produced for example from long oligonucleotides by a stepwise PCR or, in the case of conventional gene synthesis, may be ordered from specialist suppliers (e.g. Geneart GmbH, Qiagen AG).

Surprisingly, the expression of the corresponding gene can be negatively influenced (smaller number of CpG) or positively influenced (increased number of CpG) by suitably choosing the number of CpG dinucleotides, and may even exceed the expression rates that can be achieved with a codon-optimised gene. The expression may unexpectedly even be raised if the increase in the number of CpG dinucleotides takes place at the expense of the RNA and codon optimisation. Preferably no CpG islands are introduced in the modification of the target nucleic acid sequence, and preferably the modified target nucleic acid sequence is not associated with CpG islands. By way of delimitation as regards the defined CpG islands, whose influence on the expression operates according to the all-or-none principle, in the present invention a correlation is found between the level of expression and the number of CpG dinucleotides.

For the expression of genes these modifications are preferably introduced so that the coded amino acid sequence is not altered. In the ideal case only the nucleic acid sequence of a corresponding gene should influence its level of expression. Since the genetic code is degenerate, there is the possibility, for a specific amino acid sequence, of choosing a plurality of corresponding nucleic acid sequences.

By way of delimitation as regards the hitherto described methods, 1) the region coding for the transcript should be modified, whereby this method can be used independently of vectors and other gene technology conditions, and 2) for an increase in the level of expression the number of CpG dinucleotides should be raised. The additionally introduced CpGs are in this connection not methylated.

Preferably the number of CpG dinucleotides compared to the sequence of the target nucleic acid sequence to be expressed is increased or reduced, depending on the desired level of expression, by at least 2, preferably at least 3, more preferably at least 5, still more preferably at least 8, yet more preferably at least 10, even more preferably by at least 15, and up to 20 or more, especially by 30-50 or even up to 100 or more, depending on the length of the target nucleic acid sequence to be expressed.

Preferably the number of CpG dinucleotides compared to the sequence of the target nucleic acid to be expressed is raised by at least 10%, preferably at least 20%, more preferably at least 50%, particularly preferably at least 100%, and especially at least 200%, or by a factor of 5 or 10.

If CpGs are eliminated, it is preferred to eliminate all CpGs that can be eliminated within the scope of the genetic code. However, fewer CpGs can also be eliminated, for example 10%, 50% or 75%, in which case the elimination again depends on the desired level of expression.

Within the scope of the present invention it has surprisingly been found that increasing or reducing the number of CpG dinucleotides permits a stepwise modulation of the gene expression. A dose effect was surprisingly observed. This means that the level of gene expression can be adjusted by the addition or elimination of more or fewer CpG dinucleotides.

As already mentioned, it is possible and preferred to make use of the degeneracy of the genetic code so that preferably the maximum number of CpG dinucleotides is introduced or eliminated without having to alter the amino acid sequence of the target nucleic acid sequence to be expressed. The maximum number of CpG dinucleotides to be introduced is preferably limited by the variation possibilities of the degenerated codon of a predetermined amino acid sequence.

On the other hand, if desired the number of CpG dinucleotides may be increased still further, even if the corresponding amino acid sequence is thereby altered. In this case care should be taken to ensure that the function of the peptide or protein is not interfered with.

The CpG dinucleotides may, depending on the type of degeneracy of the genetic code, be removed or added within a codon or also overlapping a codon.

In addition to the change in the number of CpG dinucleotides in the target nucleic acid to be expressed, the latter may be changed further at the nucleic acid level depending on the desired degree of gene expression. If for example an increase in gene expression is aimed for, then the number of CpG dinucleotides is preferably raised in such a way that, due to the introduction of further CpG dinucleotides, no disadvantageous effects occur, such as for example more strongly expressed secondary structures of the mRNA, which could have a disadvantageous effect on the translation, or further motifs that could negatively influence the expression, e.g. RNA instability motifs, splice-activating motifs, endonuclease recognition sites, and the like. On the other hand it is of course also possible, if the number of CpG dinucleotides is decreased in order to reduce the gene expression, to eliminate the CpG dinucleotides specifically at those sites which, after alteration of the nucleic acid sequence, lead to specifically these motifs.

Again, it is of course also possible and also preferred, in addition to increasing or reducing the number of CpG dinucleotides, moreover to carry out a nucleic acid optimisation, so that either the gene expression is promoted or inhibited, or is reduced.

Such optimisations are accordingly the insertion or removal of motifs that can influence the gene expression, for example secondary structure-stabilising sequences, regions with raised self-homology, regions with raised homology with respect to the natural gene, RNA instability motifs, splice-activating motifs, polyadenylation motifs, adenine-rich sequence steps, endonuclease recognition sites and the like. Yet a further possible way of optimisation consists in optimising in each case the codon choice for the desired expression system.

This means that, within the scope of the present invention, the expression may also be raised or reduced if, in addition to the insertion of CpG dinucleotides, the codon choice is optimised or made worse. Expression-optimised constructs according to the invention can be produced for example by choosing the codon distribution to be the same as in the expression system that is used. Preferably the eukaryotic expression system is a mammalian system, preferably a human system. Preferably therefore the codon optimisation is matched to the codon choice of human genes. Preferably in this connection, a codon choice is used that is most frequently or next to most frequently employed in mammalian cells (Ausubel et al., 1994), in order to ensure a general stabilisation of the RNA and an optimal codon choice. Still more preferably, the nucleic acid sequence is modified for an optimal expression by using the gene optimiser technology (DE 102 60 805.9 or PCT/EP03/14850).

In contrast to the codon optimisation, "poor" codons seldom used by the expression system may however also be employed in order to increase the number of CpG dinucleotides.

In the method according to the invention a heterologous target nucleic acid sequence may also be used. The expression "heterologous target nucleic acid sequence" refers to the origin of the target nucleic acid sequence and to the origin of the expression system. Preferably therefore the target nucleic acid sequence and the expression system are heterologous to one another, i.e. they are derived either from different species and/or the codon choice of the wild-type target nucleic acid sequence is a different sequence to that of the expression system. The term "heterologous" within the context of the invention thus also includes differences with respect to the codon choice. The codon choice denotes the preferred codon usage for a respective species, within the scope of the degeneracy of the genetic code.

As expression vector there may be used any suitable expression vector. Such a vector is preferably suitable for expression in eukaryotic cells. The modified target nucleic acid sequence to be expressed is cloned into the vector so that it is in operative coupling with a suitable transcription control sequence and possibly further regulator elements. A suitable promoter, which may either be constitutive or inducible, may be such a transcription control sequence.

Constitutively active promoters are preferably selected from, but not restricted to, CMV (Cytomegalovirus) promoter and Simian Virus 40 (SV40). Inducible promoters include, but however are not restricted to, tetracyclin-dependent promoters. The person skilled in the art is capable without any difficulty of selecting further suitable promoters depending on the application, e.g. also promoters of cellular origin.

In this connection, in principle any inducible promoter system that is known in the prior art is suitable. For example, a natural or artificial inducible promoter may be used, for example a promoter inducible by tetracyclin (Tet on/Tet off system). Furthermore, an inducible viral promoter may however also be used.

Preferably the inducible promoter can be induced by a transactive factor. A viral inducible promoter which can be induced by a viral transactive factor may be derived from an arbitrary virus. Sequences of retroviruses, HCV (Hepatitis C virus), HBV (Hepatitis B virus), HSV (Herpes Simplex virus), EBV (Epstein-Barr virus), SV 40 (Simian virus 40), AAV (Adeno-associated virus), Adenovirus, Papilloma viruses or Ebola virus are preferably used for this purpose. The transactive factors used in this connection are accordingly selected for example from the following viral factors, but are not restricted to these: NS5A (HCV), HB X (HBV), VP16/ICP4 (EBV), EBNA1/Rta (EBV), ART (HHV8), Large T-Antigen (SV40), Rep78/68 (AAV), E1A (Adenovirus), E2 (Papilloma virus) and VP30 (Ebola virus).

As inducible promoter that can be induced by a viral transactive factor, there is preferably used a retroviral LTR promoter or a functional partial sequence thereof. Preferably therefore the transactive factor is a retroviral Tat or Tax protein. The LTR promoter may be selected from the LTRs of HIV-1, HIV-2, SIV, HTLV and other related retroviruses that have LTR promoters. In particular lentiviral promoters are preferred, especially those of HIV.

Preferably the transcription control sequences, i.e. for example promoters and/or enhancers, etc., used within the scope of the present invention are not associated with CpG islands.

It is also possible, in addition to increasing the number of CpG dinucleotides in the target nucleic acid to be expressed, to reduce the number of CpG dinucleotides in the remaining sequences or parts thereof present on the vector. In this connection the CpG dinucleotides in these remaining vector sequences or parts thereof may be completely eliminated. Preferably this is again carried out while retaining the amino acid sequence by utilising the degeneracy of the genetic code. Also, only a partial elimination of the CpG dinucleotides in these sequences may take place, for example of at least 5%, preferably at least 10%, more preferably at least 15%, particularly preferably at least 25%, more particularly preferably 50%, and most particularly preferably 75% or more. Preferably all CpGs are removed insofar as this is possible.

Thus, depending on the application (silencing or increasing the expression) the number of CpG dinucleotides may be varied independently of the chosen codon optimisation.

In most cases a complete elimination of CpGs from the reading frame is possible. The coded amino acid sequence is upwardly limiting, i.e. as regards increasing the number of CpGs.

The target nucleic acid sequence may code for an RNA, derivatives or mimetics thereof, a peptide or polypeptide, a modified peptide or polypeptide, a protein or a modified protein.

The target nucleic acid sequence may also be a chimera and/or assembled sequence of different wild-type sequences, and for example it may code for a fusion protein or mosaic-like constructed polygene constructs. The target nucleic acid sequence may also code for a synthetic sequence. In this connection it is also possible to model the nucleic acid sequence synthetically, for example with the aid of a computer model.

The target nucleic acid sequence to be expressed may preferably be a sequence for a gene for an arbitrary protein, for example a recombinant protein, an artificial polypeptide, a fusion protein and the like. Diagnostic and/or therapeutic peptides, polypeptides and proteins are preferred. The peptide/protein may for example be used for i) the production of therapeutic products, such as e.g. human enzymes (e.g. asparaginase, adenosine deaminase, insulin, tPA, clotting factors, vitamin K epoxide reductase), hormones (e.g. erythropoietin, follicle-stimulating hormone, oestrogens) and other proteins of human origin (e.g. bone morphogenic proteins, antithrombin), ii) viral, bacterial proteins or proteins derived from parasites, which may be used as vaccines (derived from HIV, HBV, HCV, influenza, borrelia, haemophilus, meningococcus, anthrax, botulin toxin, diphtheria toxin, tetanus toxin, plasmodium, etc.) or iii) proteins that may be used for the production of diagnostic test systems (e.g. blood group antigens, HLA proteins).

As a further possibility, a gene may be chosen that produces messenger substances (cytokines/chemokines), e.g. G-CSF, GM-CSF, interleukins, interferons, PDGF, TNF, RANTES or MIP1α or domains, fragments or variants thereof, which are capable of actuating the natural defence mechanisms of adjacent cells or, in combination with suitable antigens, of amplifying a specific immune response.

A further possible use is in the production of proteins, such as for example enzymes (polymerases, proteases, etc.) for biotechnology applications.

The target nucleic acid to be expressed may also be a regulator gene, which after its expression in a cell as a molecular switch molecule switches the expression of other genes on or off. As such a regulator gene there may for example be used a component of a signal transduction pathway or a transcription factor. The term "expression" includes in this connection the transcription of the target nucleic acids and possibly the translation of the RNA obtained by transcription.

Finally, the target nucleic acid to be expressed may be a functional RNA (e.g. ribozyme, decoy or siRNA), which may preferably be used for therapeutic or enzymatic purposes.

The present invention furthermore relates to a modified nucleic acid with a region capable of transcription, which is derived from a wild-type sequence, wherein the region capable of transcription is modified so that the number of CpG dinucleotides is increased compared to the wild-type sequence, by using the degeneracy of the genetic code. The modified nucleic acid may be expressed in an expression system as described above, and the region capable of transcription is modified so that it is codon-optimised in relation to the used expression system, and so that the number of CpG dinucleotides compared to the codon-optimised sequence derived from the wild-type sequence is raised, using the degeneracy of the genetic code.

A wild-type sequence within the meaning of the present invention is a naturally occurring nucleic acid sequence.

As already mentioned above, it is however also possible for the target nucleic acid sequence to code for an assembled gene sequence, which may be assembled from different wild-type sequences. In such a case the wild-type sequence refers to the sequence that has not yet been modified within the meaning of the present invention (increase or reduction of the number of CpG dinucleotides).

The number of CpG dinucleotides in the nucleic acid according to the invention may, as mentioned above, be increased by several CpG dinucleotides. Preferably the number is raised to the maximum number that is possible within the scope of the degeneracy of the genetic code.

The present invention also provides an expression vector, which includes an aforementioned modified nucleic acid according to the invention in operative coupling with suitable transcription control sequences. The vector is preferably used to increase the expression in eukaryotic cells of an arbitrary DNA sequence. The vector is preferably derived from known vectors. In the sequence regions of the vector that are different from the modified nucleic acid sequence according to the invention, the number of CpG dinucleotides is preferably reduced. Preferably the number of CpG dinucleotides in these remaining vector sequences or parts thereof is reduced by at least 5%, preferably at least 10%, more preferably at least 15%, still more preferably at least 25%, in particular at least 50%, and most particularly preferably at least 75% or more.

The reduction of CpGs is preferably achieved by artificial gene synthesis of the individual vector modules (antibiotic resistance gene, selection marker, multiple cloning site, etc.) as described above. The individual modules are assembled with corresponding DNA fragments of essential, non-alterable modules (replication origin, polyadenylation site, viral promoter, etc.) using singular restriction sites, to form a functional vector. The vector may be of viral (e.g. derived from adenoviruses, retroviruses, Herpes viruses, alpha viruses, etc.) or bacterial origin, or naked DNA (expression plasmids).

The modular construction of the vector moreover permits a rapid and easily effected alteration as regards the individual modules. The number of modules may be varied and adapted corresponding to the application.

For a stable integration in cells, elements such as eukaryotic selection markers (e.g resistance genes to hygromycin, zeocin, etc.; selection reporters such as GFP, LNGFR, etc.; or recombination sequences for a directed recombination) may be used, in which the corresponding gene sequences can, as far as possible, also be reduced as regards the content of CpGs. For applications in gene therapy sequences can be introduced that counteract immunostimulating motifs (e.g. immuno-repressive CpG motifs). Accordingly, for applications in immunisations, such as for example in vaccinations or for the production of antibodies, sequences may be integrated that contain immunostimulating factors (e.g. immunostimulating CpG motifs).

A preferred vector for use in the present invention is the vector illustrated in SEQ ID NO. 27.

The present invention also provides eukaryotic cells, more preferably mammalian cells, most particularly preferably human cells, that contain a target nucleic acid or a vector (preferably in the form of a DNA construct) as described above, in which the nucleic acid or the vector is present in a form capable of transcription. The cells are preferably somatic cells or, more preferably, those cells that basically do not carry out any de novo methylation.

The DNA construct may for example be present episomally or integrated stably into the chromosome. In this connection one or more copies may be present in the cell. To introduce the said DNA constructs, gene ferries of viral (e.g. adenoviruses, retroviruses, Herpes viruses, alpha viruses, etc.) or bacterial origin or naked DNA (expression plasmids) may be used.

The present invention moreover provides an expression system comprising:
a) a modified nucleic acid sequence with a region capable of transcription, which is derived from a wild-type sequence, wherein the modified nucleic acid sequence has an increased or reduced number of CpG dinucleotides compared to the wild-type sequence, in operative coupling with a transcription control sequence, and b) an expression environment selected from a cell and a cell-free expression environment wherein a) can be expressed, in which the expression system in the case of expression of a modified nucleic acid sequence with an increased number of CpG dinucleotides exhibits an increased expression, and in the case of expression of a modified nucleic acid sequence with a reduced number of CpG dinucleotides exhibits a reduced expression.

The present invention can thus be used so as to increase or reduce the expression of a target nucleic acid sequence. If the expression is raised, then preferably an increase of the expression of at least 5%, more preferably at least 10%, still more preferably at least 20%, even more preferably at least 30%, especially at least 50% and most especially at least 100-400% or more, should be achieved. Depending on the length of the target nucleic acid sequence to be expressed and the number of CpG dinucleotides that can be introduced, an increase in the expression by a factor of 2, 3, 5 or even 10 to 20, or possibly up to 100 to 200, may also be achieved.

If a reduction of the expression is desired, then preferably a reduction of the expression, in other words for example a reduction of the transcript amount of at least 10%, preferably at least 20%, more preferably at least 30%, still more preferably at least 50% and especially at least 75%, should be carried out. Preferably the expression should approach the limit of detection.

As already explained above in detail, the level of transcription depends on the number of CpG dinucleotides in the gene. This means that in the case of longer genes or in genes with more possibilities of introducing CpG dinucleotides, a higher level of expression should be achieved. Conversely, it should be possible with the aid of the present invention to reduce the expression significantly by the targeted elimination of as far as possible all CpG dinucleotides, and depending on the application even to the limit of detection.

The present invention additionally provides medicaments and diagnostic agents based on the modified nucleic acids and/or vectors according to the invention. The modified nucleic acids and vectors may be used in diagnostic, therapeutic and/or gene therapy applications, in particular also for the production of vaccines.

In particular the method according to the invention and the expression systems, nucleic acid sequences, vectors and cells according to the invention may be used for the production of DNA vaccines. As an alternative to conventional dead vaccines and living vaccines, the development of vaccines that are based on "naked" plasmid DNA is becoming increasingly important. The advantage of DNA vaccines lies in an uptake of the DNA in cells, combined with the authentic production (including modification) of antigens and an efficient activation of a cellular and humoral immune response. In this connection the level of the induced immune response correlates with the amount of antigen produced and thus with the expression output of the DNA constructs. If the expression of an arbitrary antigen can be increased by the accumulation of CpG dinucleotides in the coding sequence, then as a result the activation of the immune system and thus the protective effect is improved.

DESCRIPTION OF THE DIAGRAMS

FIG. 1:
Regulation of the gene expression by methylation (prior art).
A: Methylation of CpG dinucleotides leads to the switching off of the gene expression.
B: CpG islands protect against a methylation and the switching off associated therewith.
C: Secondary hypomethylation of the CpG islands leads to a gene switching off.
D: Secondary hypomethylation may be prevented by reducing the CpG dinucleotides in the reading frame.

Figure 2:
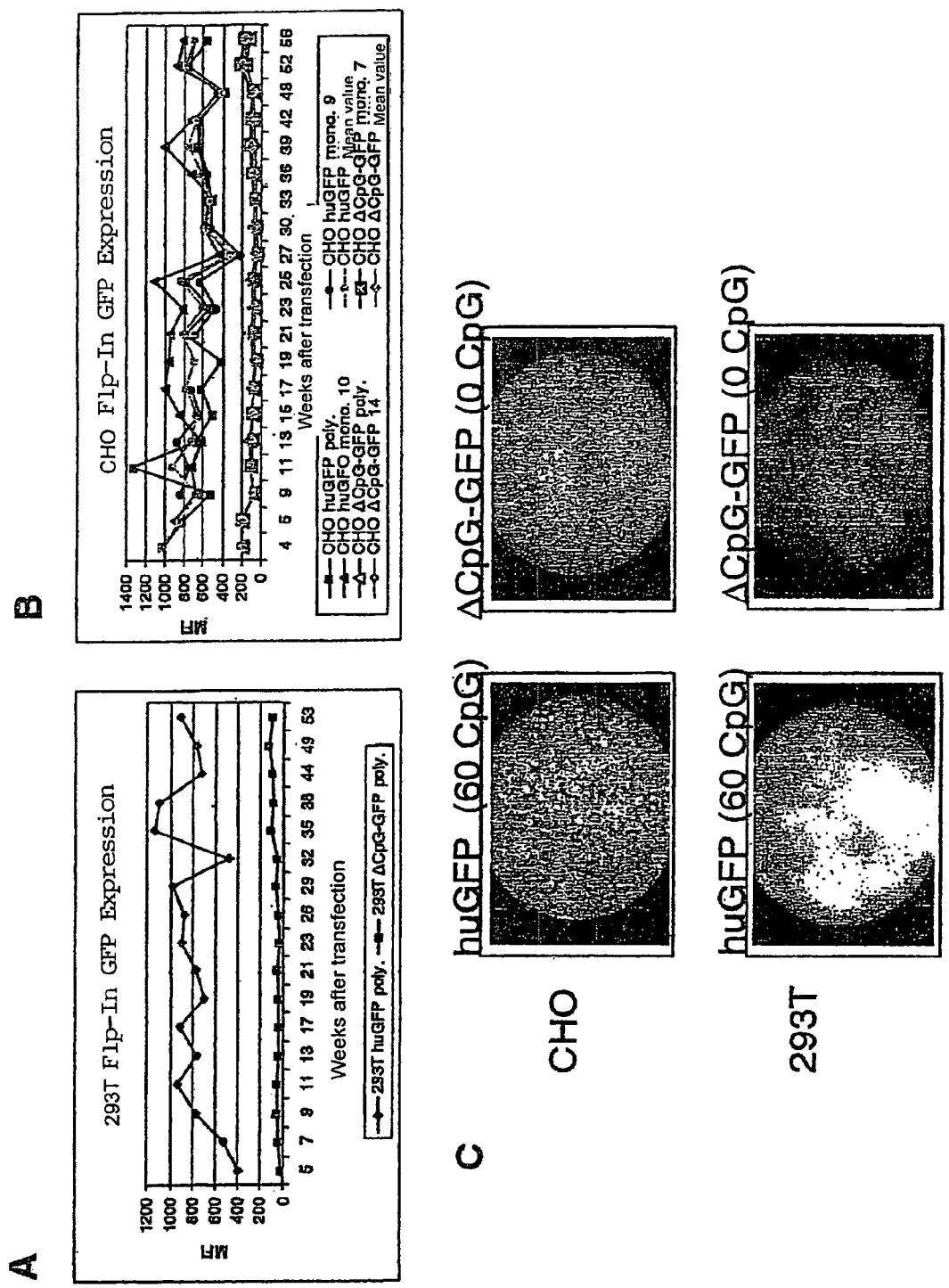

FIG. 2:
GFP expression analysis in stably transfected cells. A and B: Long-time flow cytometry analysis of stably transfected Flp-In 293T and CHO cells. The Y axis gives the GFP-conditioned fluorescence intensity (MFI "mean fluorescence intensity") and the X axis gives the measurement times in weeks after transfection.
A: FACS analysis of huGFP and ΔCpG-GFP recombinant 293T cells.
B: FACS analysis of huGFP and ΔCpG-GFP recombinant CHO cells.
C: Flourescence microscopy image of stable cell lines.

Figure 3:
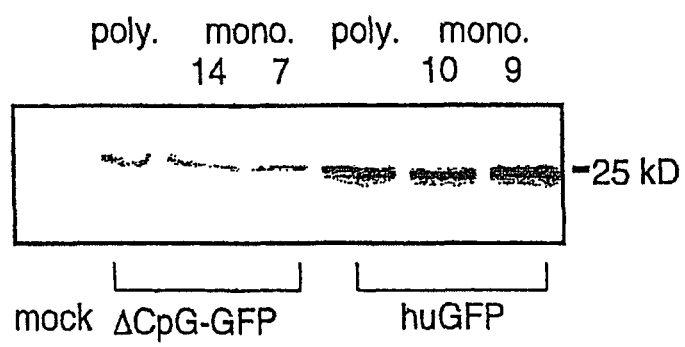

FIG. 3:
GFP protein detection in stably transfected cells. Expression analysis of the GFP reading frame. Recombinant Flp-In CHO cells that have integrated the huGFP or the ΔCpG-GFP gene stably into the cell genome were lysed, and the expression of the genes was detected by conventional immunoblot analyses. Plots of the huGHF, ΔCpG-GFP and mock samples are given. Monoclonal cell lines were established from both polyclonal cell cultures (poly.) (mono. 14 and 7 for ΔCpG-GFP and mono. 10 and 9 for huGFP). Mock cells correspond to an unchanged initial cell population.

Figure 4:
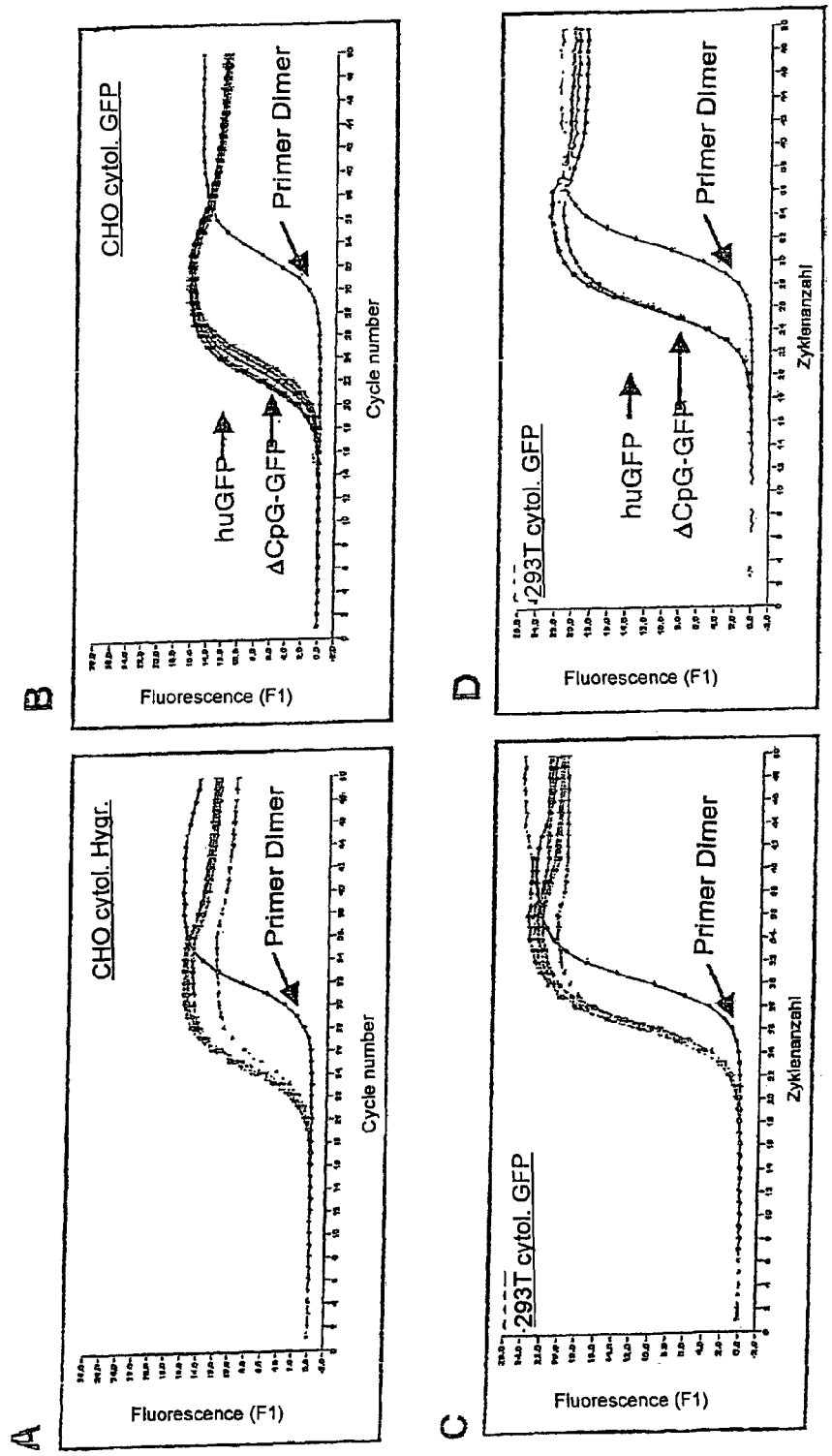

FIG. 4:
Quantitative determination of specific transcripts of stable cells. Real-time PCR analysis of specific hygromycin-resistance gene and gfp RNAs from cytoplasmic RNA preparations. The real-time PCR evaluation of the LC analyses are shown for CHO cells (hygromycin-resistance A and gfp B) as well as for 293T cells (hygromycin-resistance C and gfp D). The number of PCR cycles (X axis) and the fluorescence intensity (Y axis) are shown. The specific kinetics are shown for huGFP products and ΔCpG-GFP products, as well as for the primer dimers.

Figure 5:
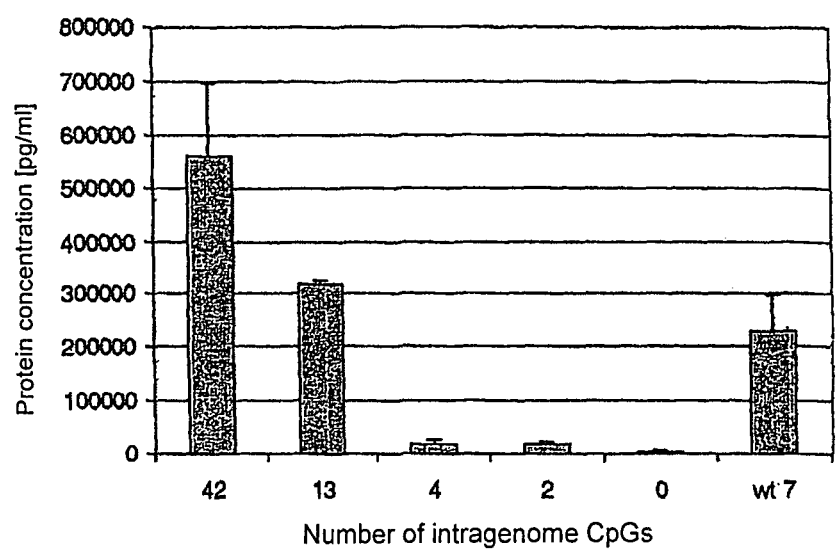

FIG. 5:
MIP1alpha expression analysis after transient transfection. Representative ELISA analysis of the cell lysates and supernatants of transfected H1299 cells. H1299 cells were transfected with in each case 15 μg of wild-type and optimised murine MIP1alpha constructs. The respective protein concentration was quantified by conventional ELISA tests in the cell supernatant and in the cell lysate with the aid of corresponding standard curves. The shaded bars represent the mean value of the total protein concentration for in each case two independent batches, while the empty bars correspond to the standard deviation. The number of CpG dinucleotides in the open reading frame is plotted on the X axis and the total protein concentration in pg/ml is plotted on the Y axis. Wt corresponds to the expression construct of the respective wild-type gene.

Figure 6:
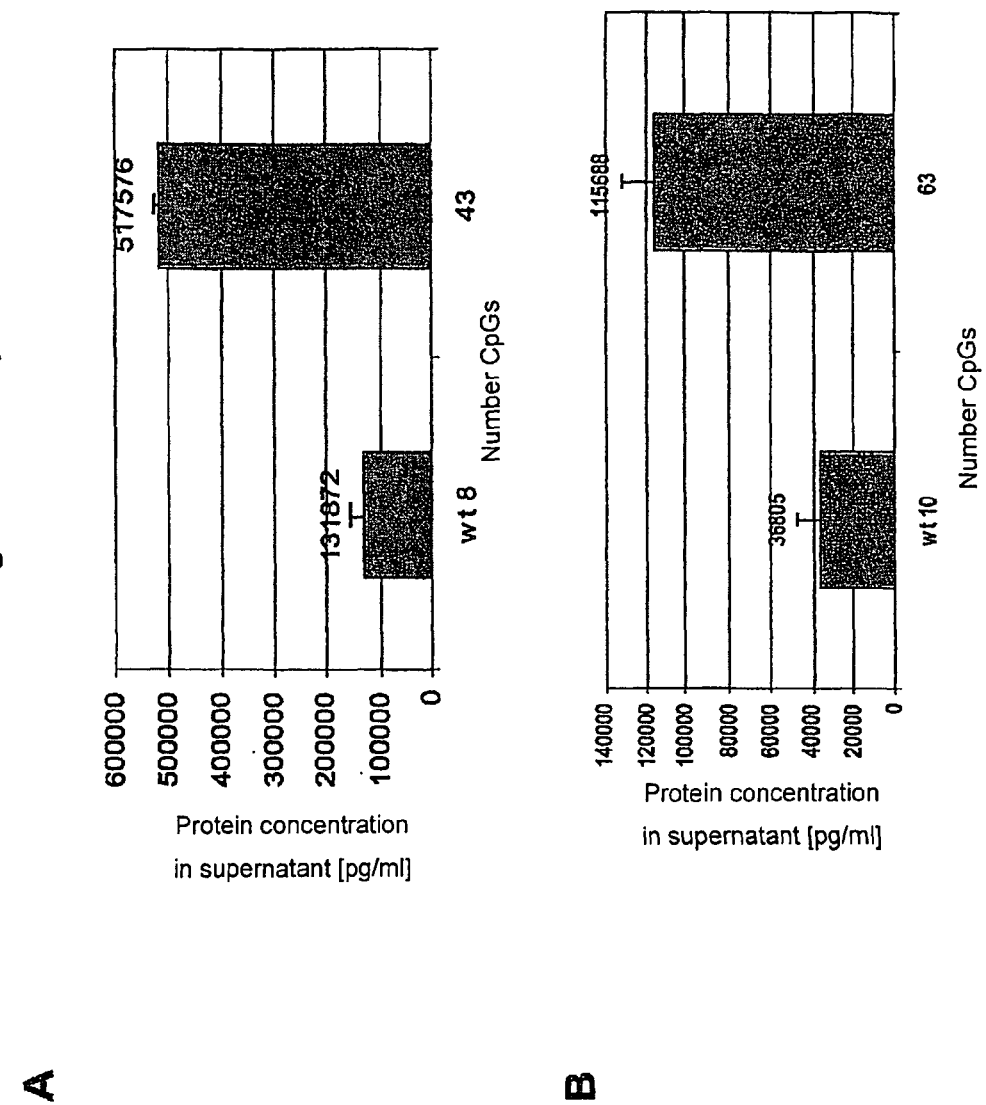

FIG. 6:
MIP1alpha and GM-CSF expression analysis after transient transfection. Representative ELISA analysis of the supernatants of transfected H1299 cells. H1299 cells were transfected with in each case 15 μg of wild-type and optimised human MIP1alpha (A) and GM-CSF (B) constructs. The respective protein concentration in the supernatant of the cell culture 48 hours after transfection was quantified by conventional ELISA tests with the aid of corresponding standard curves. The shaded bars represent the mean value for in each case two independent batches, while the empty bars correspond to the standard deviation. The number of CpG dinucleotides in the open reading frame is plotted on the X axis and the protein concentration in the supernatant in pg/ml is plotted on the Y axis. Wt corresponds to the expression construct of the respective wild-type gene.

FIG. 7:

Diagrammatic illustration of the used expression plasmids.
A: Plasmid map of the P-smallsyn plasmid.
B: Plasmid map of the PC-ref. module and origin of the sequences (wild-type "Wt" in black, and synthetic in grey) are shown.

FIG. 8:

HIV-1 p24 detection after transient transfection. Expression analysis of the P-smallsyn and Pc-ref vectors. H1299 cells were transfected with the specified constructs and the protein production was detected by conventional immunoblot analyses. Analysis of the cell lysates of HIV-1 p24 transfected H1299 cells. Molecular weights (precision plus protein standard, Bio-Rad) as well as the plot of the R/p24, s/p24 and mock-transfected samples are shown. Mock transfection corresponds to a transfection with the original pcDNA3.1 plasmid.

FIG. 9:

HIV-1 p24 expression analysis of various expression constructs. H1299 cells were transfected with in each case 15 μg R/p24, R/24ΔCpG, s/p24 and s/p24ΔCpG constructs, as well as with pcDNA3.1 (mock control) in independent double batches. The respective p24 protein concentration in the cell lysate was quantified by conventional immunoblot analyses (A) and by ELISA tests (B) with the aid of corresponding standard curves. The shaded bars represent the mean value of the p24 concentration (in μg/ml) in the cell lysate for in each case 2 independent batches.

EXAMPLES

Example 1

Production of GFP Reporter Genes with Different CpG Content

Two variants of green fluorescence protein (GFP) genes, which differ in the number of CpG dinucleotides, were produced. The huGFP gene had 60 CpGs, the ΔCpG-GFP gene had no CpGs. The CpG-depleted gene ΔCpG-GFP was constructed artificially. In the design of the ΔCpG-GFP care was taken to ensure that no rare codons or negatively acting cis-active elements such as splicing sites or poly(A) signal sites were introduced. The codon adaptation index (CAI), which is a measure of the quality of the codon choice, was altered only slightly by the deletion of the CpGs (CaI(huGFP)=0.95; CAI (ΔCpG-GFP)=0.94). The coding amino acid sequence of the GFP was in this connection not altered. Further interfaces were inserted for the sub-cloning. The nucleotide and amino acid sequences are given in SEQ ID NO. 1/2.

The sequence was produced as a fully synthetic gene (Geneart GmbH), cloned into the expression vector pcDNA/5FRT (Invitrogen) using the interfaces HindIII and Bam HI, and placed under the transcription control of the cytomegalovirus (CMV) early promoter/enhancer ("pc ΔCpG-GFP").

For the production of a similar expression plasmid, though unchanged in its CpG content, the coding region of the humanised GFP gene (huGFP) was amplified by means of a polymerase chain reaction (PCR) using the oligonucleotides huGFP-1 and huGFP-2 from a commercially obtainable vector, and likewise cloned into the expression vector pcDNA/5FRT ("pc-huGFP", SEQ ID NO. 3/4) using the interfaces HindIII and Bam HI.

Production of Stable Cell Lines with the GFP Gene variants

The Flp-In system of Invitrogen was used for a rapid establishment and selection of stable, recombinant cells. A further, major advantage of this system is a directed integration of a copy of the transgene into a defined locus of the target cell. This technology thus provides the best conditions for the quantitative comparison of the expression of an arbitrary transgene, since physiological and genetic factors of the target cell are largely identical. In order to achieve an additional certainty, two different mammalian cells were selected for these comparative analyses. The cell lilnes Fip-In CHO and Fip-In 293T were obtained from Invitrogen and cultured at 37° C. and 5% $CO_2$. The cell lines were cultured in Dulbecco's modified eagle medium high glucose (DMEM) (293T) and HAMs F12 (CHO) with L-glutamine, 10% inactivated fetal bovine serum, penicillin (100 U/ml) and streptomycin (100 μg/ml). The cells were sub-cultured in a ratio of 1:10 after confluence was achieved.

The establishment of stably transfected cells was carried out according to the manufacturer's instructions. $2.5 \times 10^5$ cells were seeded out in 6-well culture dishes and transfected 24 hours later by calcium phosphate co-precipitation (Graham and Eb, 1973) with 1.5 μg transfer plasmid and 13.5 μg pOG44. Cells were selected up to a ratio of >90% GFP positive cells with 100 μg/ml hygromycin for 293T and 500 μg/ml for CHO cells. The number of GFP positive cells was determined for all cell lines by means of conventional flow cytometry analysis.

Determination of the GFP Expression

The expression of the reporter constructs was determined over a period of 16 months by regular measurement of the GFP-mediated green autofluorescence in a flow cytometer (Becton-Dickinson). The data of the mean fluorescence intensities are summarised in FIGS. 2A (293T cells) and 2B (CHO cells). The huGFP expression was found to e relatively constant in both cell lines over the whole measurement period, with a mean fluorescence intensity of 800 (293T) and 700 (CHO). The ΔCpG-GFP reporter construct, with a reduced number of CpGs, likewise exhibited a constant fluorescence intensity over the whole measurement period. The mean fluorescence intensity was however reduced by a factor of 10-20 (293T) and 6-9 (CHO) compared to the huGFP. The reduction of the GFP-mediated fluorescence could also be detected by fluorescence microscopy (FIG. 2C).

Since various causes may be involved in a decrease of the GFP-mediated fluorescence (instability of the protein, reduced nuclear export of RNA, lower transcription rate, etc.) additional western blot analyses and quantitative real-time PCRs were carried out.

For the protein detection by immunoblot, the stable transfected CHO cells were washed twice with ice-cold PBS (10 mM $Na_2HP_4$, 1.8 mM $KH_2PO_4$, 137 mM NaCl, 2.7 mM KCl), scraped off in ice-cold PBS, centrifuged for 10 minutes at 300 g, and lysed for 30 minutes in lysis buffer on ice (50 mM Tris-HCl, pH 8.0, 0.5% Triton X-100 (w/v)). Insoluble constituents of the cell lysate were centrifuged for 30 minutes at 10000 g and 4° C. The total amount of protein in the supernatant was determined by the Bio-Rad protein assay (Bio-Rad, Munich) according to the manufacturer's instructions.

An equal volume of two-fold sample buffer (Laemmli, 1970) was added to the samples, and heated for 5 minutes at 95° C. 40 µg of total protein from cell lysates were separated through a 12.5% SDS/polyacrylamide gel (Laemmlie, 1970), electrotransferred to a nitrocellulose membrane and detected with a monoclonal GFP-specific antibody (BD-Bioscience) and a secondary, HRP (horseradish peroxidase) coupled antibody, and identified by means of chromogenic staining. Protein detection by western blot confirmed the data from the FACS measurement. For both gene variants the full-length GFP protein was detected in stably transfected CHO cells; no differences could be detected in the processing or proteolytic degradation (FIG. 3).

In order to clarify the transcription activity, a quantitative real-time PCR (Light Cycler, Roche) was carried out for the stably transfected CHO cells. Cytoplasmic RNA was prepared from the cells (RNeasy, Quiagen) and treated with DNase (500 U Rnase-free DNase/20 µg RNA). 1 µg of the DNase-treated RNA was used as a matrix for a reverse transcription (Random Primed, $p(dN)_6$, $1^{st}$ strand C-DNA synthesis kit for RT-PCR, Roche) followed by PCR (RT-oligo1 and RT-oligo2). The resulting PCR product was diluted and used for a light cycler (LC) analysis (SYBR, Roche). As internal control, the RNA amount of the hygromycin-resistance gene similarly integrated into the cell genome was measured. The results are summarised in FIG. 4. The RNA amounts of the hygromycin-resistance showed no difference in all the measured constructs (FIGS. 4A for CHO cells and 4C for 293T cells). The results of the GFP RNA however correlated very well with the results of the protein expression (GFP fluorescence intensity). For the CpG-deleted construct, after quantification of the light cycler data an approximately seven times smaller cytoplasmic RNA amount was detected in CHO cells (FIG. 4B) and an approximately thirty times smaller RNA amount was detected in 293T cells (FIG. 4D), compared to the initial construct.

Example 2

Production of Murine Mip1alpha Genes with Different CpG Contents

In this example the nucleic acid sequence of the murine MiP1alpha gene was altered so as to form a series of constructs with different numbers of CpG dinucleotides, but without altering the coding amino acid sequence. For this purpose the amino acid sequence of the murine MIP1alpha gene product was translated back into synthetic MIP1alpha-coding reading frames, using the codon choice of human cells. In a first series of constructs the accidentally formed CpG dinucleotides were removed stepwise from the sequence, without however introducing rare codons that would be expected to adversely affect the expression. In addition a CpG dinucleotide-optimised Mip1alpha gene construct was produced, which contained twice as many CpG dinucleotides as the codon-optimised construct. In this case a deterioration of the codon choice was intentionally taken into account, in order to introduce as many CpG dinucleotides as possible. According to the prior art it would be expected that this gene construct would have a lower expression than the codon-optimised gene construct on account of its poorer codon choice.

These gene variants were constructed as fully synthetic reading frames, using long oligonucleotides and a stepwise PCR, and cloned into an expression vector. The produced MIp1alpha vector variants differed completely as regards the level of expression of murine MIP1alpha. For the person skilled in the art it could not be foreseen that the variants with the lowest CpGs would be expressed worst, and an increase in the CpGs would be accompanied by an increase of the MiP1alpha expression in mammalian cells. In particular it could not be foreseen by the person skilled in the art that the construct with the maximum possible number of CpG dinucleotides, which however were introduced at the expense of a deterioration of the codon choice, exhibited a significantly stronger expression than the codon-optimised gene.

Variants of the murine Mip1alpha gene that differ in the number of CpG dinucleotides were synthetically constructed as described in Example 1 and sub-cloned into the expression vector pcDNA3.1 using the interfaces HindIII and NotI. The artificially produced genes were in each case matched as regards their codon choice to the mammalian system. When removing the CpG dinucleotides no rare mammalian codons were used, whereas when inserting CpG dinucleotides above the number of dinucleotides that are achieved with a normal codon adaptation, rare codons were intentionally also employed.

The constructs that are codon optimised but provided with different numbers of CpG dinucleotides, have throughout a CAI value of more than 0.9 and differ only slightly. The CAI values of the wild-type gene, as well as of the CpG dinucleotide optimised gene (42 CpGs) have on the other hand very low CAI values (below 0.8). According to the prior art a comparable expression of the codon-optimised genes would therefore be expected, though a significantly lower expression of the wild-type gene and of the CpG dinucleotide optimised gene. The identification of the constructs, the number of CpGs as well as the CAI values are given in Table 1. The nucleotide and amino acid sequences are given in SEQ ID NO. 5/6 to SEQ ID NO. 13/14. The analogous expression construct (wild-type reference construct) corresponding to the wild-type sequence was unchanged as regards its CpG distribution. The coding region was amplified by means of a polymerase chain reaction (PCR) using the oligonucleotides mamip-1 and mamip-2 from a cDNA clone (obtained from RZPD) and likewise cloned into the expression vector pcDNA3.1 using the interfaces HindIII and NotI ("pc-mamip-wt", SEQ ID NO. 15, GenBank Accession Number AA071899).

Checking the Mip1alpha Expression

In order to quantify the chemokine expression, human H1299 cells were transfected with the respective expression constructs and the amount of protein in the cells and in the cell culture supernatant was measured by means of commercial ELISA test kits.

$1.5 \times 10^5$ human lung carcinoma cells (H1299) were seeded out in 6-well cell culture dishes and transfected 24 hours later by calcium phosphate precipitation with 15 µg of the corresponding expression plasmid. The cells and cell culture supernatant were harvested 48 hours after the transfection. The transfected cells were lysed as described in Example 1 and the total amount of protein of the cell lysate was determined with the Bio-Rad protein assay. Insoluble cell constituents were removed from the cell culture supernatant by centrifugation at 10000 g for 15 minutes at 4° C.

From 1-5 µg total protein from cell lysates as well as from diluted cell culture supernatants, the expression of MiP1alpha was checked in each case in a commercially obtainable ELISA assay (R & D Systems) according to the manufacturer's instructions. The total amount of detectable MiP1alpha correlated with the number of CpGs in the reading frame, in a comparable manner to the data of the GFP expression constructs and p24 expression constructs. The data are summarised in Table 1. The number of constructs permitted for the first time a detailed evaluation of the connection of the level of expression with the number of CpGs within the coding region.

A representative result of an evaluation by means of cytokine ELISA is shown in FIG. 5. The shaded bars correspond to the mean value of two independent transfection batches, while the empty bars represent the respective standard deviations.

The relative protein amounts of two independent transient transfection experiments (in double batches) referred to the wild-type construct are listed in Table 1. These results demonstrate a marked reduction of the protein expression with the decrease in CpG dinucleotides and a marked increase compared to the wild-type gene and to the codon-optimised genes, correlating with the additional introduction of such motifs and despite a deterioration of the codon matching.

TABLE 1

Expression comparison of murine MIP1alpha genes

| Construct | SEQ ID NO. | Expression* | St. Dev.** | CpG No. | CAI*** |
|---|---|---|---|---|---|
| pc-maMIP wt | 15 | 100% | 4% | 8 | 0.76 |
| pc-maMIP 0 | 5 | 2% | 9% | 0 | 0.92 |
| pc-maMIP 2 | 7 | 8% | 27% | 2 | 0.93 |
| pc-maMIP 4 | 9 | 7% | 33% | 4 | 0.93 |
| pc-maMIP 13 | 11 | 146% | 5% | 13 | 0.97 |
| pc-maMIP 42 | 13 | 246% | 4% | 42 | 0.72 |

*Percentage mean value of the amount of protein from 2 tests (in double batches) in relation to the total amount of protein of the wild-type construct (maMIP wt)
**Standard deviation
***Codon adaptation index Example 3

Production of Human and Murine Cytokine Genes with Different CpG Contents

In order to be able to further confirm the hitherto obtained results and interpretations, variants of the human MIP1alpha gene, of the human GM-CSF gene, of the human IL-15 gene and of the murine GM-CSF gene, which differ in the number of CpG dinucleotides from the wild-type gene, were artificially constructed similarly to Example 2 and sub-cloned into the expression vector pcDNA3.1 using the interfaces HindIII and NotI. The identification of the constructs, number of CpGs as well as the CAI values are given in Table 2. The nucleotide and amino acid sequences of the wild-type sequences (wt) and of the sequences with an altered number of CpG dinucleotides are given in SEQ ID NO. 17/18 to SEQ ID NO. 23/24 and SEQ ID NO. 48/49 to SEQ ID NO. 54/55. The expression constructs were amplified by means of a polymerase chain reaction (PCR) using the oligonucleotides humip-1 and humip-2, hugm-1 and hugm-2, huil-1 and huil-2, magm-1 and magm-2 from corresponding cDNA clones (obtained from RZPD) and were cloned into the expression vector pcDNA3.1, likewise using the interfaces HindIII and NotI ("pc-huMiP-wt", GenBank Accession Number NM_021006, "pc-huGM-wt", GenBank Accession Number M11220, "pc-huIL-wt", GenBank Accession Number BC018149, "pc-muGM-wt", GenBank Accession Number NM_049969 with a deviation).

Checking the Cytokine Expression

In order to quantify the cytokine expression human cells were transfected with the respective expression constructs and the amount of protein in the cell culture supernatant was measured by means of commercial ELISA test kits.

As described in Example 2, H1299 cells were transfected transiently with 15 µg of the corresponding expression plasmid. The cell culture supernatant was harvested for 48 hours after the transfection. Insoluble cell constituents were removed from the cell culture supernatant by centrifugation.

From dilute cell culture supernatants the expression of human MIP1alpha, human GM-CSF and IL-15 and murine GM-CSF was checked in each case in a commercially obtainable ELISA assay (R & D Systems for MIP1alpha; BD Pharmingen for GM-CSF and IL-15). In a comparable way to the data of the aforementioned expression constructs, the total amount of detectable cytokines in the culture supernatant correlated with the number of CpGs in the reading frame. The data are summarised in Table 2. A representative result of an evaluation by means of cytokine ELISA is shown in FIG. 6. The shaded bars correspond to the mean value of two independent transfection batches, while the empty bars represent the respective standard deviation. The relative amounts of protein in each case from a transient transfection experiment (in double batches) referred to the wild-type construct are listed in Table 2. Similarly to the results from Example 2, these results too confirm a marked increase in protein production, correlating with the additional introduction of such motifs, compared with the wild-type genes.

TABLE 2

Expression comparison of human cytokine/chemokine genes

| Construct | SEQ ID No. | Expression* | CpG No. | CAI** |
|---|---|---|---|---|
| pc-huMiP wt | 21 | 100% | 8 | 0.76 |
| pc-huMiP 43 | 17 | 393% | 43 | 0.72 |
| pc-huGM wt | 23 | 100% | 10 | 0.82 |
| pc-huGM 63 | 19 | 327% | 63 | 0.70 |
| pc-huIL wt | 56 | 100% | 3 | 0.65 |
| pc-huIL 21 | 52 | 313% | 21 | 0.98 |
| pc-muGM wt | 58 | 100% | 11 | 0.75 |
| pc-muGM 62 | 54 | 410% | 62 | 0.75 |

*Percentage mean value of the amount of protein from in each case one experiment, in double batches, in relation to the total amount of protein of the corresponding wild-type construct (denoted wt).
**Codon adaptation index Example 4

Figure 7:
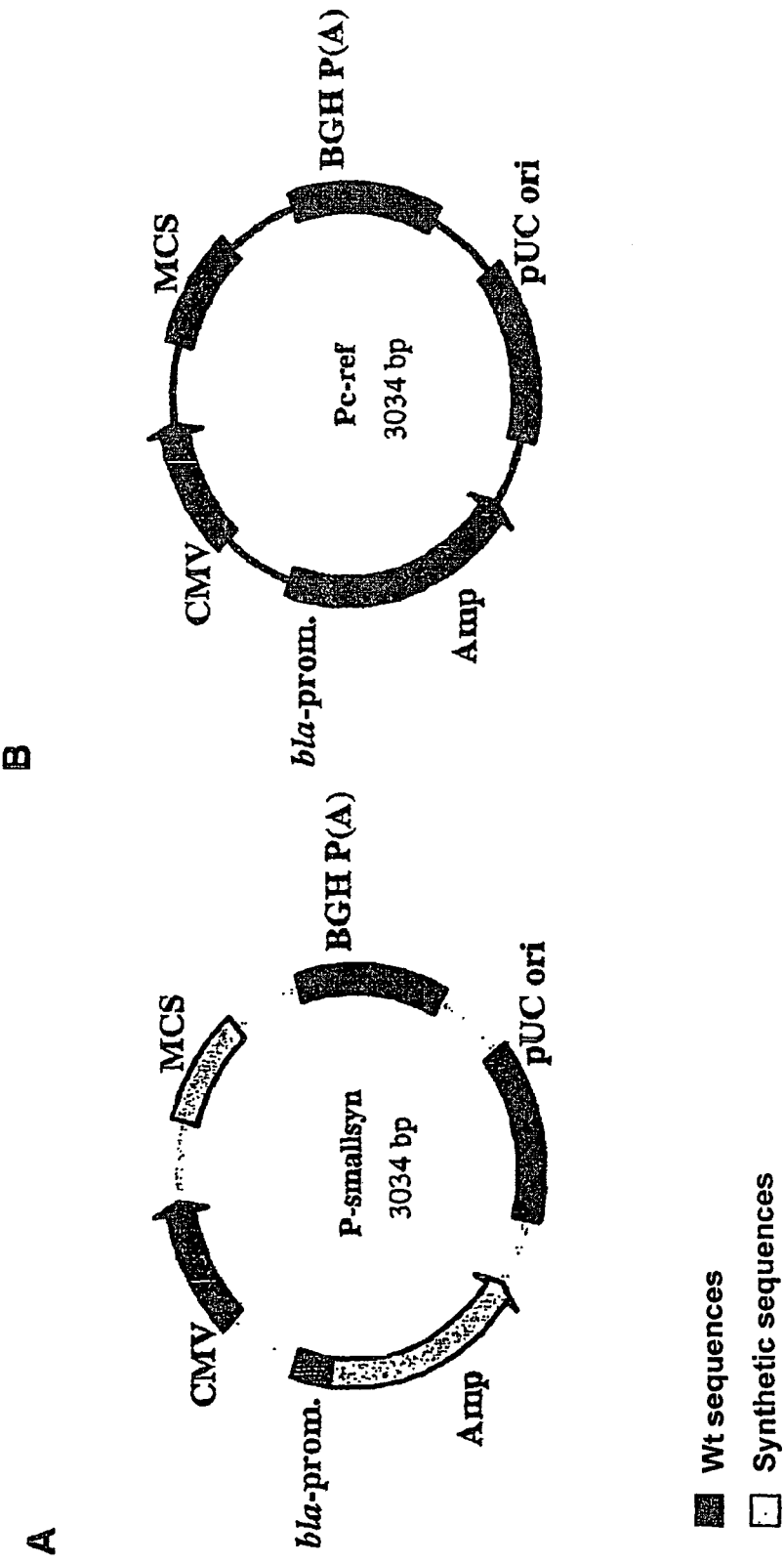

Production of a Plasmid with a Reduced Number of CpG Dinucleotides to Increase the Expression The nucleic acid sequence of the plasmid pcDNA5 (Invitrogen) was used as a basis for the production of a modularly constructed plasmid in which the number of CpG dinucleotides had been reduced as far as possible. The DNA sequence which codes for the ampicillin resistance gene (bla) was synthetically produced as described in Example 1, and sub-cloned using the restriction interfaces ClaI and BglII. The number of CpGs was in this connection reduced from 72 to 2. Likewise, the multiple cloning site was redesigned, synthetically constructed, and sub-cloned using the restriction interfaces SacI and PmeI, whereby the number of CpGs was reduced from 11 to 1. The CMV promoter (31 CpGs), the BGH polyadenylation site (3 CPGs) and the pUC replication origin (45 CpGs) were integrated unchanged into the plasmid. The hygromycin-resistance cassette was deleted. The CMV promoter was cloned by PCR amplification with the oligonucleotides CMV-1 and CMV-2, which in addition added a ClaI and a SacI restriction interface 3' and 5'. In a similar way pUC ori-1 was amplified with the oligonucleotides ori-1 (contains XmaI interface) and ori-2 (contains BglII interface), and the BGH polyadenylation site was amplified with the oligonucleotides pa-1 (PmeI) and pa-2 (XmaI) by PCR, and sub-cloned using the corresponding restriction enzymes. The plasmid pcDNA5 was used as a template in all PCR reactions. The structure of this plasmid is shown diagrammatically in FIG. 7A ("P-smallsyn"), and the complete sequence is given in SEQ ID NO. 25.

In order to investigate the influence of the number of CpGs in the vector on the level of expression of a transcript, the reference vector was modified so that it could be used as control. By PCR amplification using the oligonucleotides ref-del-1 and ref-del-2, which in each case introduced a NsiI restriction interface at the 5' end, cleavage with NsiI and ligation, the hygromycin-resistance cassette was removed from the plasmid pcDNA5 (see diagram 6B, "Pc-ref").

The p24 capsid protein derived from HIV-1 was used as test transcript. The coding region of p24 already previously optimised for expression in human cells (Graf et al., 2000) was amplified by means of PCR using the oligonucleotides p24-1 and p24-2 from an HIV-1 syngag construct (Graf et al., 2000) and cloned into the two comparison vectors using the interface HindIII and Bam HI ("R/p24" and "s/p24")

Checking the HIV-1 p24 Expression in Different Vector Backgrounds

In order to check the influence of the CpG number in the vector from the expression of the transcript, the constructs R/p24 and s/p24 were transiently transfected into human cells and the expression of p24 was analysed.

As described in Example 2, H1299 cells were transfected transiently with 15 µg of the corresponding expression plasmid. Cells were harvested 48 hours after the transfection. The transfected cells were lysed as described in Example 1 and the total amount of protein in the supernatant was determined with the Bio-Rad protein assay.

Figure 8:
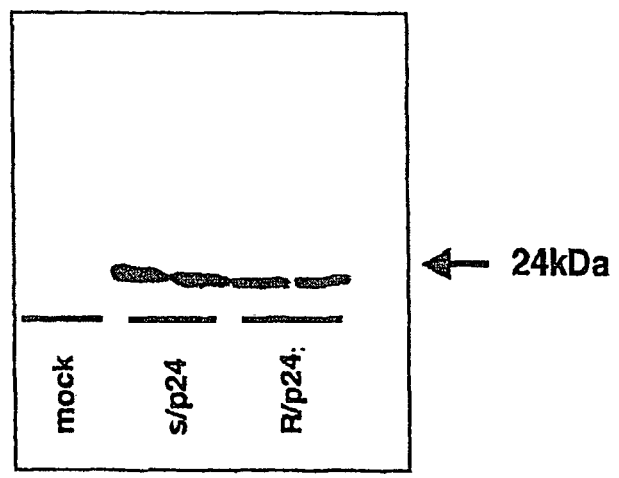

50 µg of total protein from cell lysates were tested as described in Example 1 in a western blot analysis with a monoclonal p24-specific antibody, 13-5 (Wolf et al., 1990) (FIG. 8). In two independent transfection batches a markedly higher p24 expression was detected after transfection of the smallsyn construct (s/p24).

Production of HIV p24 Genes with Different CpG Contents

Two variants of the capsid protein gene p24 derived from HIV-1, which differ in the number of CpG dinucleotides, were produced. The syn p24 gene had 38 CpGs, whereas the p24ΔCpG gene had no CpGs. The CpG-depleted gene p24ΔCpG was artificially constructed as described in Example 1 and cloned into the expression vector P-smallsyn (described in Example 4) ("s/p24ΔCpG") and into the reference vector Pc-ref ("R/p24ΔCpG") using the interfaces HindIII and Bam HI. The nucleotide and amino acid sequences of p24ΔCpG are given in SEQ ID NO. 26/27. The plasmids R/p24 and s/p24, which are described in Example 4, were used as reference constructs.

Checking the HIV-1 p24 Expression

In order to check the influence of the CpG number in the vector and in the insert (transcript), the constructs R/p24, R/p24ΔCpG, s/p24 and s/p24ΔCpG were transfected transiently into human cells and the expression of p24 was analysed.

As described in Example 2, H1299 cells were transiently transfected with 15 µg of the corresponding expression plasmid. Cells were harvested 48 hours after the transfection. The transfected cells were lysed as described in Example 1 and the total amount of protein in the lysate was determined with the Bio-Rad protein assay.

Figure 9:
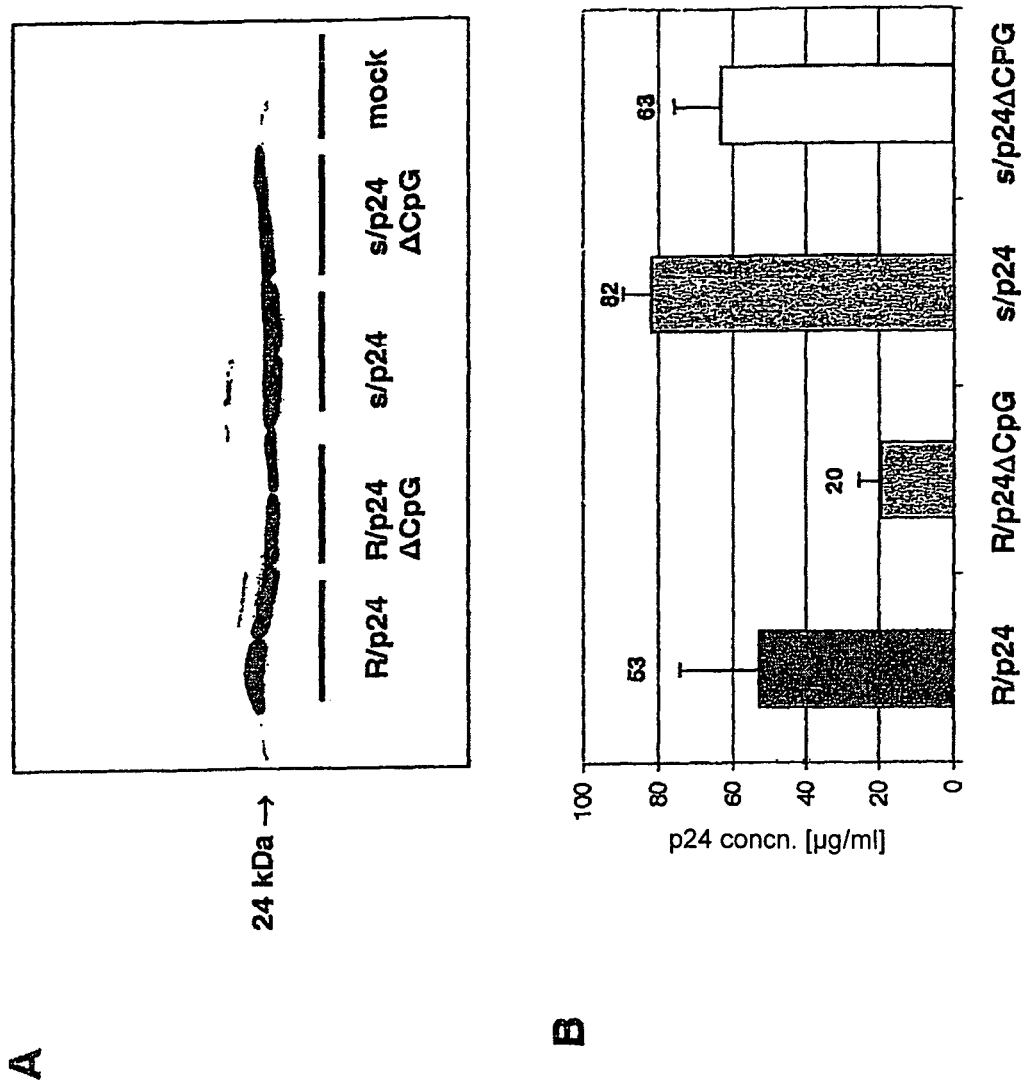

50 µg of total protein from cell lysates were checked as described in Example 1 in a western blot analysis with a monoclonal $p^{24}$-specific antibody 13-5 for the expression of p24 (FIG. 9A). As was already shown in Example 4, the use of the CpG-deleted vector P-smallsyn in the identical transgene led to a visible increase in p24 production (comparison R/p24 and s/p24). Comparably to the data of the GFP and cytokine/chemokine expression constructs, the amount of detectable p24 in the cell lysate, using the identical vector background, correlated with the number of CpGs in the reading frame (comparison R/24 and R/p24ΔCpG as well as s/p24 and s/p24ΔCpG). The data were confirmed in a p24-specific ELISA test (FIG. 9B). The construct with 38 CpGs (p24) had a ca. 2.5 times (Pc-ref) or ca. 25% (P/smallsyn) larger amount of p24 than the construct without CpGs (p24 DcpG). The results are illustrated in FIG. 9.

The correlation of the protein production with the number of CpG dinucleotides could be demonstrated in the Examples mentioned here. The selected genes are derived from such different organisms as a jellyfish, a human pathogenic virus, and mammals. It is therefore obvious to regard this mechanism as generally valid. The examples demonstrate furthermore that this correlation in vitro is valid both in the case of a transient transfection as well as in stable recombinant cells. The method described here, namely to alter in a targeted manner the gene expression in eukaryotes by targeted modulation of the CpG dinucleotides, both in the coding region as well as in the vector background, may consequently be used for the production of biomolecules for biotechnological, diagnostic or medical applications.

Description of the Sequences

1. Oligonucleotides

TABLE 3

| SEQ ID NO. | Identification | Sequence 5'-3' |
|---|---|---|
| 28 | huGFP-1 | CAATAAGCTTGCCACCATGGTGAGCAAGGGCGAG |
| 29 | huGFP-2 | AGTAGGATCCTATTACTTGTACAGCTCGT |
| 30 | RT-oligo1 | CCCTGAAGTTCATCTGCACC |
| 31 | RT-oligo2 | GATCTTGAAGTTCACCTTGATG |
| 32 | mamip-1 | CAGGTACCAAGCTTATGAAGGTCTCCACCACTGC |
| 33 | mamip-2 | CAGAGCTCGAGTCATGAAGACTAGGCATTCAGTTCCAGGTCAG |
| 34 | hugm-1 | CAGGTACCAAGCTTATGTGGCTGCAGAGCCTGC |
| 35 | hugm-2 | CAGAGCTCGAGTCATGAAGACTACTCCTGGACTGGCTCCCAGC |

TABLE 3-continued

| SEQ ID NO. | Identification | Sequence 5'-3' |
|---|---|---|
| 36 | humip-1 | CAGTACCAAGCTTATGCAGGTCTCCACTGCTGC |
| 37 | humip-2 | CAGAGCTCGAGTCATGAAGACTAGGCACTCAGCTCCAGGTCACTG |
| 38 | p24-1 | ACTAGGTACCATCTAAGCTTATGCCCATCGTGCAGAACATCCA |
| 39 | p24-2 | TCAAGAGCTCGACTGGATCCTATTACAGCACCCTGGCCTTGTGGC |
| 40 | CMV-1 | CAAAGGTACCGTTAATCGATGTTGACATTGATTATTGACTA |
| 41 | CMV-2 | GAATGAGCTCTGCTTATATAGACC |
| 42 | ori-1 | GTCACCCGGGTAGTGAATTCATGTGAGCAAAAGGC |
| 43 | ori-2 | GATCTTTTCTACGGGAGATCTGTCAATCGATAGCT |
| 44 | pa-1 | GTTAGAGCTCCAGTGTTTAAACCTGTGCCTTCTAGTTGCCAG |
| 45 | pa-2 | CAAACCTACCGATACCCGGGCCATAGAGCCCACCGCATC |
| 46 | ref-del-1 | TCAGATGCATCCGTACGTTAACATGTGAGCAAAAGGCCAGCA |
| 47 | ref-del-2 | AGTCATGCATCCATAGAGCCCACCGCATCCCCA |
| 48 | huil-1 | CAGGTACCAAGCTTATGAGAATTTCGAAACCAC |
| 49 | huil-2 | CAGAGCTCGAGTCATGAAGACTAAGAAGTGTTGATGAACATTTGG |
| 50 | magm-1 | CAGGTACCAAGCTTATGGCCCACGAGAGAAAGGC |
| 51 | magm-2 | CAGAGCTCGAGTCATGAAGACTATTTTTGGCCTGGTTTTTTGC |

2. Polypeptide-Coding Sequences and Vector Sequences

SEQ ID NO. 1 + 2:
ΔCpG-GFP (nucleic acid + polypeptide)
ATGGTGTCCAAGGGGAGGAGCTGTTCACAGGGGTGGTGCCCATCCTGGT

GGAGCTGGATGGGGATGTGAATGGCCACAAGTTCTCTGTGTCTGGGGAG

GGGAGGGGGATGCCACCTATGGCAAGCTCACCCTGAAGTTCATCTGCACC

ACAGGCAAGCTGCCAGTGCCCTGGCCCACCCTGGTGACCACCTTCACCTA

TGGGGTGCAGTGCTTCAGCAGATACCCAGACCACATGAAGCAGCATGACT

TCTTCAAGTCTGCCATGCCTGAGGGCTATGTGCAGGAGAGGACCATCTTC

TTCAAGGATGATGGCAACTACAAGACCAGGGCTGAGGTGAAGTTTGAGGG

GGATACCCTGGTGAACAGGATTGAGCTGAAGGGCATTGACTTTAAGGAGG

ATGGCAATATCCTGGGCCACAAGCTGGAGTACAACTACAACAGCCACAAT

GTGTACATCATGGCAGACAAGCAGAAGAATGGCATCAAGGTGAACTTCAA

GATCAGGCACAACATTGAGGATGGCTCTGTGCAGCTGGCAGACCACTACC

AGCAGAACACCCCCATTGGAGATGGCCCTGTCCTGCTGCCAGACAACCAC

TACCTGAGCACCCAGTCTGCCCTGAGCAAGGACCCCAATGAGAAGAGGGA

CCACATGGTGCTGCTGGAGTTTGTGACAGCTGCTGGCATCACCCTGGGCA

TGGATGAGCTGTACAAGTGA

SEQ ID NO. 3 + 4:
huGFP (nucleic acid + polypeptide)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCTTCACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA

SEQ ID NO. 5 + 6:
murine MIP1alpha-0 CpG (nucleic acid + polypeptide)
ATGAAGGTGAGCACAACAGCTCTGGCTGTGCTGCTGTGTACCATGACCCT

GTGCAACAGGTGTTCTCTGCCCCTTATGGAGCAGATACCCCTACAGCCTG

CTGTTTCAGCTACAGCAGGAAGATCCCCAGGCAGTTCATTGTGGACTACT

TTGAGACCAGCAGCCTGTGTTCTCAGCCTGGGGTGATCTTTCTGACCAAG

AGGAACAGGCAGATCTGTGCAGACAGCAAGGAGACATGGGTGCAGGAGTA

CATCACAGACCTGGAGCTGAATGCCTAG

SEQ ID NO. 7 + 8:
murine MIP1alpha-2 CpG(nucleic acid + polypeptide)
ATGAAGGTGAGCACAACAGCTCTGGCCGTGCTGCTGTGTACCATGACCCT

GTGCAACCAGGTGTTCTCTGCCCCTTATGGAGCAGATACCCCTACAGCCT

GCTGTTTCAGCTACAGCAGGAAGATCCCCAGGCAGTTCATCGTGGACTAC

TTTGAGACCAGCAGCCTGTGTTCTCAGCCTGGGGTGATCTTTCTGACCAA

GAGGAACAGGCAGATCTGTGACAGACAGCAAGGAGACATGGGTGCAGGAG

TACATCACAGACCTGGAGCTGAATGCCTAG

SEQ ID NO. 9 + 10:
murine MIP1alpha-4CpG (nucleic acid + polypeptide)
ATGAAGGTGAGCACAACAGCTCTGGCCGTGCTGCTGTGTACCATGACCCT

GTGCAACCAGGTGTTCTCTGCCCCTTACGGAGCAGATACCCCTACAGCCT

GCTGTTTCAGCTACAGCAGGAAGATCCCCAGGCAGTTCATCGTGGACTAC

TTTGAGACGAGCAGCCTGTGTTCTCAGCCTGGGGTGATCTTTCTGACCAA

-continued
GAGGAACCGCCAGATCTGTGCAGACAGCAAGGAGACATGGGTGCAGGAGT

ACATCACAGACCTGGAGCTGAATGCCTAG

SEQ ID No. 11 + 12:
murine MIP1alpha-13CpG (nucleic acid +
polypeptide)
ATGAAGGTGAGCACCACAGCTCTGGCTGTGCTGCTGTGCACCATGACCCT

GTGCAACCAGGTGTTCAGCGCTCCTTACGGCGCCGATACCCCTACAGCCT

GCTGCTTCAGCTACAGCAGGAAGATCCCCAGGCAGTTCATCGTGGACTAC

TTCGAGACCAGCAGCCTGTGTTCTCAGCCCGGCGTGATCTTCCTGACCAA

GCGGAACAGACAGATCTGCGCCGACAGCAAGGAGACATGGGTGCAGGAGT

ACATCACCGACCTGGAGCTGAACGCCTAG

SEQ ID NO. 13 + 14:
murine MIP1alpha-42CpG (nucleic acid +
polypeptide)
ATGAAGGTGTCGACGACCGCGCTCGCCGTGCTGCTGTGCACGATGACGCT

GTGCAACCAGGTGTTCAGCGCCCCGTACGGCGCCGACACGCCGACCGCGT

GCTGCTTCTCGTACTCGCGGAAGATCCCGCGGCAGTTCATCGTCGACTAC

TTCGAAACGTCGTCGCTGTGCTCGCAGCCCGGCGTGATCTTCCTCACGAA

GCGGAACCGGCAGATCTGCGCCGACTCGAAGGAAACGTGGGTGCAGGAGT

ACATCACCGACCTCGAACTGAACGCGTAG

SEQ ID NO. 15 + 16:
murine MIP1alpha wild-type (7 CPG) (nucleic acid +
polypeptide)
ATGAAGGTCTCCACCACTGCCCTTGCTGTTCTTCTCTGTACCATGACACT

CTGCAACCAAGTCTTCTCAGCGCCATATGGAGCTGACACCCCGACTGCCT

GCTGCTTCTCCTACAGCCGGAAGATTCCACGCCAATTCATCGTTGACTAT

TTTGAAACCAGCAGCCTTTGCTCCCAGCCAGGTGTCATTTTCCTGACTAA

GAGAAACCGGCAGATCTGCGCTGACTCCAAAGAGACCTGGGTCCAAGAAT

ACATCACTGACCTGGAACTGAATGCCTAG

SEQ ID NO. 17 + 18:
human MIP1alpha-43CpG (nucleic acid + polypeptide)
ATGCAAGTGTCGACCGCCGCTCTCGCCGTGCTGCTGTGCACGATGGCGCT

GTGCAACCAAGTGCTGAGCGCGCCTCTCGCCGCCGACACGCCGACCGCGT

GCTGCTTCTCGTACACGTCGCGGCAGATCCCGCAGAACTTCATCGCCGAC

TACTTCGAGACGTCGTCGCAGTGCTCGAAGCCGAGCGTGATCTTCCTGAC

GAAGCGCGGACGGCAAGTGTGCGCCGACCCGAGCGAGGAGTGGGTGCAGA

AGTACGTGAGCGACCTCGAACTGAGCGCGTAG

SEQ ID NO. 19 + 20:
human GM-CSF-63CpG (nucleic acid + polypeptide)
ATGTGGCTGCAGTCGCTGCTGCTGCTCGGAACCGTCGCGCGTGTTCGATCAG

CGCGCCTGCGCGGTCGCCGTCGCCGTCGACGCAGCCGTGGGAGCACGTGA

ACGCGATCGAGGAGGCGCGACGGCTGCTGAACCTGTCGCGCGATACAGCC

GCCGAGATGAACGAGACCGTCGAGGTGATCAGCGAGATGTTCGACCTGCA

GGAGCCGACGTGCCTGCAGACGCGGCTCGAACTGTATAAGCAGGGCCTCC

GCGGCTCGCTCACGAAGCTGAAGGGCCCGCTCACGATGATGGCGTCGCAC

TACAAGCAGCACTGCCCGCCGACGCCGGAAACGTCGTGCGCGACGCAGAT

-continued
CATCACGTTCGAGTCGTTCAAGGAGAACCTGAAGGACTTCCTGCTCGTGA

TCCCGUCGATTGCTGGGAGCCCGTGCAGGAGTAG

SEQ ID NO. 21 + 22:
human MIP1alpha wild-type (8CpG) (nucleic acid +
polypeptide)
ATGCAGGTCTCCACTGCTGCCCTTGCCGTCCTCCTCTGCACCATGGCTCT

CTGCAACCAGGTCCTCTCTGCACCACTTGCTGCTGACACGCCGACCGCCT

GCTGCTTCAGCTACACCTCCCGACAGATTCCACAGAATTTCATAGCTGAC

TACTTTGAGACGAGCAGCCAGTGCTCCAAGCCCAGTGTCATCTTCCTAAC

CAAGAGAGGCCGGCAGGTCTGTGCTGACCCCAGTGAGGAGTGGGTCCAGA

AATACGTCAGTGACCTGGAGCTGAGTGCCTAG

SEQ ID NO. 23 + 24:
human GM-CSF wild-type (10CpG) (nucleic acid +
polypeptide)
ATGTGGCTGCAGAGCCTGCTGCTCTTGGGCACTGTGGCCTGCAGCATCTC

TGCACCCGCCCGCTCGCCCAGCCCCAGCACGCAGCCCTGGGAGCATGTGA

ATGCCATCCAGGAGGCCCGGCGTCTCCTGAACCTGAGTAGAGACACTGCT

GCTGAGATGAATAAACAGTAGAAGTCATCTCAGAAATGTTTGACCTCCAG

GAGCCGACCTGCCTACAGACCCGCCTGGAGCTGTACAAGCAGGGCCTGCG

GGGCAGCCTCACCAAGCTCAAGGGCCCCTTGACCATGATGGCCAGCCACT

ACAAGCAGCACTGCCCTCCAACCCCGGAAACTTCCTGTGCAACCCAGATT

ATCACCTTTGAAAGTTTCAAAGAGAACCTGAAGGACTTTCTGCTTGTCAT

CCCCCTTTGACTGCTGGGAGCCAGTCCAGGAGTAG

SEQ ID NO. 25:
P-smallsyn (nucleic acid sequence of the plasmid)
ATCGATGTTGACATTGATTATTGACTAGTTATTAATAGTAATCAATTACG

GGGTCATTAGTTCATAGCCCATATATGGAGTTCCGCGTTACATAACTTAC

GGTAAATGGCCCGCCTGGCTGACCGCCCAACGACCCCCGCCCATTGACGT

CAATAATGACGTATGTTCCCATAGTAACGCCAATAGGGACTTTCCATTGA

CGTCAATGGGTGGAGTATTTACGGTAAACTGCCCACTTGGCAGTACATCA

AGTGTATCATATGCCAAGTACGCCGCCTATTGACGTCAATGACGGTAAAT

GGCCCGCCTGGCATTATGCCCAGTACATGACCTTATGGGACTTTCCTACT

TGGCAGTACATCTACGTATTAGTCATCGCTATTACCATGGTGATGCGGTT

TTGGCAGTACATCAATGGGCGTGGATAGCGGTTTGACTCACGGGGATTTC

CAAGTCTCCACCCCATTGACGTCAATGGGAGTTTGTTTTGGCACCAAAAT

CAACGGGACTTTCCAAAATGTCGTAACAACTCCGCCCCATTGACGCAAAT

GGGCGGTAGGCGTGTACGGTGGGAGGTCTATATAAGCAGAGCTCTCTGGC

TAACTAGAGAACCCACTGCTTACTGGCTTATCTAAATTAATACGACTCAC

TATAGGGAGACCCAAGCTGTTAAGCTTGGTAGATATCAGGGATCCACTCA

GCTGATCAGCCTCCAGTTTAAACCTGTGCCTTCTAGTTGCCAGCCATCTG

TTGTTTGCCCCTCCCCCGTGCCTTCCTTGACCCTGGAAGGTGCCACTCCC

ACTGTCCTTTCCTAATAAAATGAGGAAATTGCATGGCATTGTCTGAGTAG

GTGTCATTCTATTCTGGGGGGTGGGGTGGGGCAGGACAGCAAGGGGGAGG

ATTGGGAAGACAATAGCAGGCATGCTGGGGATGCGGTGGGCTCTATGGCC

CGGGTAGTGAATTCATGTGAGCAAAAGGCCAGCAAAAGGCCAGGAACCGT

-continued

```
AAAAAGGCCGCGTTGCTGGCGTTTTTCCATAGGCTCCGCCCCCTGACGA
GCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAG
ACACGACTTATCGCCACTGGCAGCAGCCACTGGTAACAGGATTAGCAGAG
CGAGGTATGTAGGCGGTGCTACAGAGTTCTTGAAGTGGTGGCCTAACTAC
GGCTACACTAGAAGGACAGTATTTGGTATCTGCGCTCTGCTGAAGCCAGT
TACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAA
AAAAGGATCTCAAGAAGATCCTTTGATCTTTTCTACGGGAGATCTGTCTG
ACTCTCAGTGGAACCAAAACTCATGTTAAGGGATTTTGGTCATGAGATTA
TCAAAAAGGATCTTCACCTAGATCCTTTTAAATTAAAAATGAAGTTTTAA
ATCAATCTAAAGTATATATGAGTAAACTTGGTCTGACAGGTTAACTTACC
AATGCTTAATCAATGAGGCACCAATCTCTGCAATCTGCCTATTTCTCTCA
TCCATGGTTGCCTGACTGCCTGTGGTGTAGATAACTACAATCCTGGAGGG
CTTACCATCTGGCCCCAGTGCTGCAATGATACCTCTAGACCCTCTCTCAC
CTGCTCCAGATTTATCTGCAATGAACCAGCCAGCTGGAAGGGCAGACCTC
AGAAGTGGTCCTGCAACTTTATCTGCCTCCATCCAGTCTATTAATTGTTG
TCTGGAAGCTAGAGTAAGCAGTTCACCAGTTAATAGTTTCCTCAAGGTTG
TTGCCATTGCTACAGGCATGGTGGTGTCCCTCTCATCATTTGGTATGGCT
TCATTCAGCTCTGGTTCCCATCTATCAAGCCTAGTTACATGATCACCCAT
GTTGTGCAAAAAGCAGTCMCTCCTTTGGTCCTCCAATGGTTGTCAAAAG
TAAGTTGGCAGCAGTGTTATCACTCATGGTTATGGCAGCACTGCATAATT
CTCTTACTGTCATGCCATCTGTAAGATGCTTTTCTGTGACTGGACTGTAC
TCAACCAAGTCATTCTGAGAATAGTGTATTCTTCTACCCAGTTGCTCTTG
CCCAGCATCAATTCTGGATAATACTGCACCACATAGCAGAACTTTAAAGG
TGCTCATCATTGGAAATCTTTCTTCTGGTCTAAAACTCTCAAGGATCTTA
CCAGAGTTGAGATCCAGTTCAATGTAACCCACTCTTGCACCCAACTGATC
TTCAGCATCTTTTACTTTCACCAGGGTTTCTGGGTGAGCAAAAACAGGAA
GGCAAAAGGCAGCAAAAAAGGGAATAAGGGCAACTCTGAAATGTTGAATA
CTCATAGTACTACTCTTCCTTTTTCAATATTATTGAAGCATTTATCAGGG
TTATTGTCTCATGAGCGGATACATATTTGAATGTATTTAGAAAAATAAAC
AAATAGGGGTATGCATTCAGCTCACATTTCCCTGAAAAGTGCCACCTGAA
ATTGACTGATAGGGAGTTCTCCCAATCCCTATGGTGCACTCTCAGTACA
ATCTGCTCTGATGCCTCATAGTTAAGCCAGTATCTGCTCCCTGCTTGTGT
GTTGGAGGTCACTGAGTAGTGGGCTAGCAAAATTTAAGCTACAACAAGGC
AAGGCTTGACCTACAATTGCATGAAGAATCTGCTTAGGGTTAGGCCTTTT
GCACTGCTTGGAGATGTACTGGCCAGATATACTA
```

SEQ ID NO. 26 + 27:
p24ΔCpG (nucleic acid + polypeptide)

```
ATGGTGCACCAGGCCATCAGCCCCAGGACCCTGAATGCCTGGGTGAAGGT
GGTGGAGGAGAAGGCCTTCAGCCCTGAGGTGATCCCCATGTTCTCTGCCC
TGTCTGAGGGGGCCACCCCCCAGGACCTGAACACCATGCTGAACACAGTG
GGGGGCCACCAGGCTGCCATGCAGATGCTGAAGGAAACCATCAATGAGGA
GGCTGCTGAGTGGGACAGAGTGCACCCTGTGCATGCTGGCCCCATTGCCC
CTGGCCAGATGAGGGAGCCCAGGGGCTCTGACATTGCTGGCACCACCTCC
ACCCTGCAGGAGCAGATTGGCTGGATGACCAACAACCCCCCCATCCCTGT
GGGGGAGATCTACAAGAGATGGATCATCCTGGGCCTGAACAAGATTGTGA
GGATGTACAGCCCCACCTCCATCCTGGACATCAGGCAGGGCCCCAAGGAG
CCCTTCAGGGACTATGTGGACAGGTTCTACAAGACCCTGAGGGCTGAGCA
GGCCAGCCAGGAGGTGAAGAACTGGATGACAGAGACCCTGCTGGTGCAGA
ATGCCAACCCTGACTGCAAGACCATCCTGAAGGCCCTGGGCCCAGCTGCC
ACCCTGGAGGAGATGATGACAGCCTGCCAGGGGGTGGGAGGCCCTGGCCA
CAAGGCCAGGGTGCTGTAA
```

SEQ ID NO. 52 + 53:
human IL-15-21 CpG

```
ATGCGGATCAGCAAGCCCCACCTGAGGAGCATCAGCATCCAGTGCTACCT
GTGCCTGCTGCTGAACAGCCACTTCCTGACAGAGGCCGGCATCCACGTGT
TTATCCTGGGCTGCTTCTCTGCCGGCCTGCCTAAGACAGAGGCCAACTGG
GTGAACGTGATCAGCGACCTGAAGAAGATCGAGGACCTGATCCAGAGCAT
GCACATCGACGCCACCCTGTACACAGAGAGCGACGTGCACCCTAGCTGTA
AGGTGACCGCCATGAAGTGCTTCCTGCTGGAGCTGCAGGTGATCAGCCTG
GAGAGCGGCGATGCCAGCATCCACGACACCGTGGAGAACCTGATCATCCT
GGCCAACAACAGCCTGAGCAGCAACGGCAATGTGACCGAGAGCGGCTGCA
AGGAGTGTGAGGAGCTGGAGGAGAAGAACATCAAGGAGTTCCTGCAGAGC
TTCGTGCACATCGTGCAGATGTTCATCAACACCAGCTAG
```

SEQ ID NO. 54 + 55:
murine GM-CSF-62CpG

```
ATGTGGCTGCAGAACCTGCTGTTCCTCGGCATCGTCGTGTACTCGCTGAG
CGCGCCGACGCGCTCGCCGATCACCGTGACGCGGCCGTGGAAGCACGTCG
AGGCGATCAAGGAGGCGCTGAACCTGCTCGACGACATGCCCGTGACGCTG
AACGAGGAGGTCGAGGTCGTGTCGAACGAGTTCTCGTTCAAGAAGCTGAC
GTGCGTGCAGACGCGGCTGAAGATCTTCGAGCAGGGCCTGCGCGGCAACT
TCACGAAGCTGAAGGGCGCGCTGAACATGACCGCGTCGTACTACCAGACG
TACTGCCCGCCGACGCCCGAGACCGATTGCGAGACGCAGGTGACGACGTA
CGCCGACTTCATCGACTCGCTGAAGACGTTCCTGACCGACATCCCGTTCG
AGTGCAAGAAGCCCGGCCAGAAGTAG
```

SEQ ID NO. 56 + 57:
human IL-15 wild-type (3CpG)

```
ATGAGAATTTCGAAACCACATTTGAAGAAGTATTTCCATCCAGTGCTACTT
GTGTTTACTTCTAAACAGTCATTTTCTAACTGAAGCTGGCATTCATGTCT
TCATTTTGGGCTGTTTCAGTGCAGGGCTTCCTAAAACAGAAGCCAACTGG
GTGAATGTAATAAGTGATTTGAAAAAAATTGAAGATCTTATTCAATCTAT
```

```
-continued
GCATATTGATGCTACTTTATATACGGAAAGTGATGTTCACCCCAGTTGCA

AAGTAACAGCAATGAAGTGCTTTCTCTTGGAGTTACAAGTTATTTCACTT

GAGTCCGGAGATGCAAGTATTCATGATACAGTAGAAAATCTGATCATCCT

AGCAAACAACAGTTTGTCTTCTAATGGGAATGTAACAGAATCTGGATGCA

AAGAATGTGAGGAACTGGAGGAAAAAAATATTAAAGAATTTTTGCAGAGT

TTTGTACATATTGTCCAAATGTTCATCAACACTTCTTAG

SEQ ID NO. 58 + 59:
murine GM-CSF-wild-type (11CpG)
ATGTGGGTGCAGAATTTACTTTTCCTGGGCATTGTGGTCTACAGCCTCTC

AGCACCCACCCGCTCACCCATCACTGTCACCCGGCCTTGGAAGCATGTAG

AGGCCATCAAAGAAGCCCTGAACCTCCTGGATGACATGCCTGTCACATTG

AATGAAGAGGTAGAAGTCGTCTCTAACGAGTTCTCCTTCAAGAAGCTAAC

ATGTGTGCAGACCCGCCTGAAGATATTCGAGCAGGGTCTACGGGCAATT

TCACCAAACTCAAGGGCGCCTTGAACATGACAGCCAGCTACTACCAGACA

TACTGCCCCCCAACTCCGGAAACGGACTGTGAAACACAAGTTACCACCTA

TGCGGATTTCATAGACAGCCTTAAAACCTTTCTGACTGATATCCCCTTTG

AATGCAAAAAACCAGGCCAAAAATAG
```

REFERENCES

Akiyama, Y., Maesawa, C., Ogasawara, S., Terashima, M. and Masuda, T. (2003) Cell-type-specific repression of the maspin gene is disrupted frequently by demethylation at the promoter region in gastric intestinal metaplasia and cancer cells, Am. J. Pathol. 163, 1911-1919.

Antequera, F. and Bird, A. (1993) Number of CpG islands and genes in human and mouse, Proc. Natl. Acad. Sci. U.S.A 90, 11995-11999.

Ausubel, F. M., Brent, R., Kingston, R. E., Moore, d. d., Seidman, J. G., Smith, J. A. and Struhl, K. (1994) Percentage of Kodon Synonymous Usage and Frequency of Kodon Occurrence in Various Organisms, Current Protocols in Molecular Biology 2, A1.8-A1.9.

Bird, K P. (1980) DNA methylation and the frequency of CpG in animal DNA, Nucleic Acids Res. 8, 1499-1504.

Chevalier-Mariette, C., Henry, I., Monffort, L., Capgras, S., Forlani, S., Muschler, J. and Nicolas, J. F. (2003) CpG content affects gene silencing in mice: evidence from novel transgenes, Genome Biol. 4, R53.

Choi, Y. S., Kim, S., Kyu, L. H., Lee, K. U. and Pak, Y. K. (2004) In vitro methylation of nuclear respiratory factor-1 binding site suppresses the promoter activity of mitochondrial transcription factor A, Biochem. Biophys. Res. Commun. 314, 118-122.

Deml L., Bolak A., Steck S., Graf M., Wild J., Schirmbeck R., Wolf H., Wagner R. (2003) Multiple Effects of Codon Usage Optimization on Expression and Immunognicity of DNA Candidate Vaccines Encoding the Human Immunodeficiency Virus Type 1 Gag Gene, J. Virol. 75 No. 22, 10999-11001.

Deng, G., Chen, A., Pong, E. and Kim, Y. S. (2001) Methylation in hMLH1 promoter interferes with its binding to transcription factor CBF and inhibits gene expression, Oncogene 20, 7120-7127.

Duan J. and Antezana A. (2003) Mammalian Mutation Pressure, Synonymous Codon Choice, and mRNA Degradation, J. Mol. Evol. 57, 694-701

Hendrich, B. and Bird, A. (1998) Identification and characterization of a family of mammalian methyl-CpG binding proteins, Mol. Cell Biol. 18, 6538-6547.

Hisano, M., Ohta, H., Nishimune, Y. and Nozaid, M. (2003) Methylation of CpG dinucleotides in the open reading frame of a testicular germ cell-specific intronless gene, Tact1/Actl7b, represses its expression in somatic cells, Nucleic Acids Res. 31, 4797-4804.

Hsieh, C. L. (1994) Dependence of transcriptional repression on CpG methylation density, Mol. Cell Biol. 14, 5487-5494.

Ivanova, T., Vinokurova, S., Petrenko, A., Eshilev, E., Solovyova, N., Kisseljov, F. and Kisseljova, N. (2004) Frequent hypermethylation of 5' flanking region of TIMP-2 gene in cervical cancer, Int. J. Cancer 108, 882-888.

Jones, P. L., Veenstra, G. J., Wade, P. A., Vermaak, D., Kass, S. U., Landsberger, N., Strouboulis, J. and Wolffe, A. P. (1998) Methylated DNA and MeCP2 recruit histone deacetylase to repress transcription, Nat. Genet. 19, 187-191.

Kang, G. H., Lee, S., Lee, H. J. and Hwang, K. S. (2004) Aberrant CpG island hypermethylation of multiple genes in prostate cancer and prostatic Intraepithelial neoplasia, J. Pathol. 202, 233-240.

Kudo, S. (1998) Methyl-CpG-binding protein MeCP2 represses Sp1-activated transcription of the human laukosialin gene when the promoter is methylated, Mol. Cell Biol. 18, 5492-5499.

Laemmli, U. K. (1970) Cleavage of structural proteins during the assembly of the head of bacteriophage T4, Nature 227, 680-685.

Larsen, F., Gundersen, G., Lopez R. and Prydz H. (1992) CpG islands as gene markers in the human genome, Genomics 13, 1095-1107.

Li, Q. L., Kim, H. R., Kim, W. J., Choi, J. K., Lee, Y. H., Kim, H. M., Li, L. S., Kim, H., Chang, J., Ito, Y., Youl, L. K. and Bae, S. C. (2004) Transcriptional silencing of the RUNX3 gene by CpG hypermethylation is associated with lung cancer, Biochem. Biophys. Res. Commun. 314, 223-228.

Nan, X., Ng, H. H., Johnson, C. A., Laherty, C. D., Turner, B. M., Elsenman, R. N. and Bird, A. (1998) Transcriptional repression by the methyl-CpG-binding protein MeCP2 involves a histone deacetylase complex, Nature 393, 386-389.

Shen, J. C., Rideout W. M., III and Jones, P. A. (1994) The rate of hydrolytic deamination of 5-methylcytosine in double-stranded DNA, Nucleic Acids Res. 22, 972-976.

Sved, J. and Bird, A. (1990) The expected equilibrium of the CpG dinucleotide in vertebrate genomes under a mutation model, Proc. Natl. Acad. Sci. U.S.A 87, 4692-4696.

Takei, D. and Jones, P. A. (2002) Comprehensive analysis of CpG islands in human chromosomes 21 and 22, Proc. Natl. Acad. Sci. U.S.A 99, 3740-3745.

Voo, K. S., Carlone, D. L., Jacobsen, B. U., Flodin, A., and Skalnik, D. (2000) Cloning of a Mammalian Transcriptional Activator That Binds Unmethylated CpG motifs and Shares a CXXC Domain with DNA Mathyltransferase, Human Trithorax, and Methyl-CpG Binding Domain Protein 1, Mol. And Cell. Biol. March 2000, 2108-2121.

Wade, P. A., Gegonne, A., Jones, P. L., Ballestar, E., Aubry, F. and Wolffe, A. P. (1999) Mi-2 complex couples DNA methylation to chromatin remodelling and histone deacetylation, Nat. Genet. 23, 62-66.

Wise, T. L. and Pravtcheva, D. D. (1999) The undermethylated state of a CpG island region in igf2 transgenes is dependent on the H19 enhancers, Genomics 60, 258-271.

Wolf, H., Modrow, S., Soutschek, E., Motz, M., Grunow, R. and Döbl, H. (1990) Production, mapping and biological characterisation of monoclonal antibodies to the core protein (p24) of the human immunodeficiency virus type 1, AIFO 1, 24-29.

Wu, Q., Shi, H., Suo, Z. and Nesland, J. M. (2003) 5'-CpG island methylation of the FHIT gene is associated with reduced protein expression and higher clinical stage in cervical carcinomas, Ultrastruct. Pathol. 27, 417-422.

Yao, X., Hu, J. F., Daniels, M., Shiran, H., Zhou, X., Yan, H., Lu, H., Zeng, Z., Wang, Q., Li, T. and Hoffman, A R. (2003) A methylated oligonucleotide inhibits IGF2 expression and enhances survival in a model of hepatocellular carcinoma, J. Clin. Invest 111, 265-273.

Yoshida, M., Nosaka, K., Yasunaga, J. I., Nishikata, I., Morishita, K. and Matsuoka, M. (2003) Aberrant expression of the MEL1S gene identified in association with hypomethylation in adult T-cell leukemia cells, Blood.

---

The invention claimed is:

1. An isolated nucleic acid molecule having a region capable of transcription, codon-optimized relative to an expression system, wherein the number of CpG dinucleotides is increased compared to the codon-optimized sequence without altering the amino acid sequence encoded by said isolated nucleic acid molecule.

2. The isolated nucleic acid molecule of claim 1, comprising increasing the number of CpG dinucleotides by at least 10%.

3. The isolated nucleic acid molecule of claim 1, wherein the nucleic acid molecule is not associated with a CpG island.

4. The isolated nucleic acid molecule of claim 1, comprising a nucleotide sequence selected from the group consisting of: SEQ ID NOs. 1, 5, 7, 9, 13, 17, 19, 26, 52 and 54.

5. An expression vector comprising the isolated nucleic acid molecule of claim 1 operatively coupled with a transcription control sequence.

6. The expression vector of claim 5 wherein the transcription control sequence comprises a promoter.

7. The expression vector of claim 6, wherein the promoter is a constitutively active promoter.

8. The expression vector of claim 7, wherein the constitutively active promoter is cytomegalovirus (CMV) promoter or Simian virus 40 (SV40) promoter.

9. The expression vector of claim 6, wherein the promoter is an inducible promoter.

10. The expression vector of claim 9, wherein the inducible promoter is a tetracyclin-dependent promoter.

11. The expression vector of claim 5, wherein the promoter is not associated with a CpG island.

12. An expression vector comprising the isolated nucleic acid molecule of claim 1 operatively coupled with a transcription control sequence, wherein at least one portion of said expression vector that is not said isolated nucleic acid molecule has a reduced number of CpG dinucleotides in said at least one portion.

13. The expression vector of claim 12, comprising reducing the number of CpG dinucleotides in said at least one portion by about 25%.

14. The expression vector of claim 5, comprising the isolated nucleic acid molecule of SEQ ID NO. 25.

15. A cell containing the nucleic acid molecule of claim 1.

16. A cell transformed or transfected with the expression vector of claim 5.

17. An expression system comprising:
(a) an isolated nucleic acid molecule having a region capable of transcription, codon-optimized in relation to the expression system, and having a modified number of CpG dinucleotides compared to the codon-optimized sequence, operatively coupled to a transcription control sequence, and
(b) an expression environment selected from a cell and a cell-free expression environment, wherein (a) can be expressed, wherein expression of said isolated nucleic acid molecule having an increased number of CpG dinucleotides results in increased expression and expression of said nucleic acid molecule having a reduced number of CpG dinucleotides results in reduced expression.

* * * * *